United States Patent
Boyle et al.

(10) Patent No.: US 9,161,924 B2
(45) Date of Patent: Oct. 20, 2015

(54) FACTOR IXA INHIBITORS

(75) Inventors: Craig Boyle, Branchburg, NJ (US); William Greenlee, Teaneck, NJ (US); Samuel Chackalamannil, Califon, NJ (US); Claire Lankin, High Bridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/131,469

(22) PCT Filed: Jul. 3, 2012

(86) PCT No.: PCT/US2012/045348
§ 371 (c)(1),
(2), (4) Date: Apr. 15, 2014

(87) PCT Pub. No.: WO2013/009527
PCT Pub. Date: Jan. 17, 2013

(65) Prior Publication Data
US 2014/0219989 A1 Aug. 7, 2014

Related U.S. Application Data

(60) Provisional application No. 61/505,647, filed on Jul. 8, 2011.

(51) Int. Cl.
| | |
|---|---|
| C07D 261/20 | (2006.01) |
| A61K 31/423 | (2006.01) |
| A61K 31/167 | (2006.01) |
| C07D 215/38 | (2006.01) |
| C07D 217/22 | (2006.01) |
| C07D 401/12 | (2006.01) |
| C07D 239/42 | (2006.01) |
| C07D 295/192 | (2006.01) |
| C07C 257/18 | (2006.01) |
| C07C 235/38 | (2006.01) |
| A61K 31/47 | (2006.01) |
| A61K 31/472 | (2006.01) |
| A61K 31/505 | (2006.01) |
| A61K 31/506 | (2006.01) |
| A61K 31/5375 | (2006.01) |
| A61K 31/5377 | (2006.01) |
| A61K 45/06 | (2006.01) |
| C07C 235/16 | (2006.01) |

(52) U.S. Cl.
CPC ............ *A61K 31/167* (2013.01); *A61K 31/423* (2013.01); *A61K 31/47* (2013.01); *A61K 31/472* (2013.01); *A61K 31/505* (2013.01); *A61K 31/506* (2013.01); *A61K 31/5375* (2013.01); *A61K 31/5377* (2013.01); *A61K 45/06* (2013.01); *C07C 235/16* (2013.01); *C07C 235/38* (2013.01); *C07C 257/18* (2013.01); *C07D 215/38* (2013.01); *C07D 217/22* (2013.01); *C07D 239/42* (2013.01); *C07D 261/20* (2013.01); *C07D 295/192* (2013.01); *C07D 401/12* (2013.01)

(58) Field of Classification Search
CPC ............................ C07D 261/20; A61K 31/423
USPC ........................ 544/137; 546/272.1; 548/241; 514/233.8, 338, 339, 379
See application file for complete search history.

(56) References Cited

U.S. PATENT DOCUMENTS

| | | | |
|---|---|---|---|
| 4,386,080 A | 5/1983 | Crossley et al. | |
| 6,683,211 B1 | 1/2004 | Lamberth et al. | |
| 7,678,913 B2 | 3/2010 | Song et al. | |
| 2011/0059958 A1 | 3/2011 | Nishida et al. | |

FOREIGN PATENT DOCUMENTS

| | | |
|---|---|---|
| WO | WO2009075874 A1 | 6/2009 |
| WO | WO2009143039 A2 | 11/2009 |
| WO | WO2010065717 A1 | 6/2010 |
| WO | WO2011017296 A1 | 2/2011 |
| WO | WO2011025565 A1 | 3/2011 |
| WO | WO2013063068 A1 | 5/2013 |

OTHER PUBLICATIONS

Eikelboom et al., Coagulation Factor IXa as a Target for Treatment and Prophylaxis of Venous Thromboembolism, Arterioscler Thromb Vasc Biol. 30, pp. 382-387 (2010).*
Gura, Systems for identifying New Drugs are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
PCT Search Report and Written Opinion mailed on Sep. 17, 2012 for PCT/US2012/45348, 8 pages.
Extended European Search Report for 12811069.9 mailed Apr. 20, 2015; pp. 4.

\* cited by examiner

*Primary Examiner* — Deepak Rao
(74) *Attorney, Agent, or Firm* — Nicole M. Beeler; Catherine D. Fitch

(57) ABSTRACT

The present invention provides a compound of Formula (I) as described herein, or a pharmaceutically acceptable salt thereof. The present invention also provides pharmaceutical compositions comprising one or more said compounds, and methods for using said compounds for treating or preventing a thromboses, embolisms, hypercoagulability or fibrotic changes.

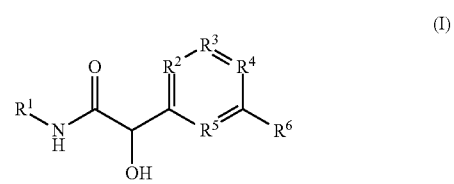

(I)

14 Claims, No Drawings

FACTOR IXA INHIBITORS

CROSS REFERENCE TO RELATED APPLICATIONS

This application is a U.S. National Phase application under 35 U.S.C. §371 of PCT Application No. PCT/US12/045348 filed Jul. 3, 2012, which claims priority from U.S. Provisional Application Ser. No. 61/505,647, filed Jul. 8, 2011.

FIELD OF THE INVENTION

The invention relates to novel compounds of the Formula (I) having antithrombotic activity which, in particular, inhibit blood clotting factor IXa, to processes for their preparation and to use thereof as medicaments.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. Clotting factor IX can be activated by means of the intrinsic pathway and the extrinsic pathway. The activation of factor IXa is thus a central point of intersection between the two pathways of activation of clotting. Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445). Vijaykumar et al., Biorganic & Medicinal Chemistry Letters (2006), 16 (10), 2796-2799, discloses hydroxy pyrazole based factor IXa inhibitors.

SUMMARY OF THE INVENTION

In its many embodiments, the present invention provides a novel class of compounds, pharmaceutical compositions comprising one or more said compounds, and methods for using said compounds, for treating or preventing thrombus formation, embolisms, hypercoagulability or fibrotic changes.

The compounds of Formula (I) according to the invention are suitable for prophylactic and for therapeutic administration to humans who suffer from diseases which accompany thromboses, embolisms, hypercoagulability or fibrotic changes. They can be employed for secondary prevention and are suitable both for acute and for long-term therapy.

The invention therefore relates to a compound of Formula (I)

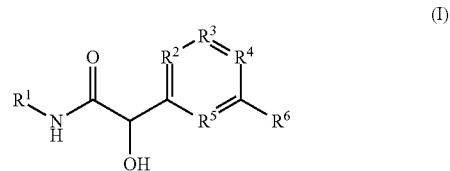

wherein
$R^1$ is
  1) an aryl ring, or
  2) a heteroaryl ring, wherein the point of attachment to the heteroaryl ring is a carbon atom, and the heteroaryl ring is selected from the group consisting of:
    a) a 5- or 6-membered unsaturated monocyclic ring with 1, 2, 3, or 4 heteroatom ring atoms selected from the group consisting of N, O or S,
    b) an 9- or 10-membered unsaturated bicyclic ring with 1, 2, 3, or 4 heteroatom ring atoms selected from the group consisting of N, O or S,
said aryl and heteroaryl ring is unsubstituted, or independently mono-, di-, or tri-substituted on any carbon ring atom with $R^7$;
$R^2$ is CH or N;
$R^3$ is CH or N;
$R^4$ is CH or N;
$R^5$ is CH, N, or $CR^8$
$R^6$ is
  1) an aryl ring, or
  2) a heteroaryl ring, wherein the point of attachment to the heteroaryl ring is a carbon atom, and the heteroaryl ring is selected from the group consisting of:
    a) a 5- or 6-membered unsaturated monocyclic ring with 1, 2, 3, or 4 heteroatom ring atoms selected from the group consisting of N, O or S,
    b) an 9- or 10-membered unsaturated bicyclic ring with 1, 2, 3, or 4 heteroatom ring atoms selected from the group consisting of N, O or S,
said aryl and heteroaryl ring is unsubstituted, or independently mono-, di-, or tri-substituted on any carbon ring atom with $R^9$;

$R^7$, each time in which it occurs, is independently —C(NR$^{11}$)N(R$^{11}$)$_2$, —N(R$^{11}$)$_2$, —CN or —C$_{1-6}$alkyl, wherein alkyl is unsubstituted or substituted at any carbon atom with —NH$_2$;

$R^8$ is hydrogen, halogen or C$_{1-6}$ alkyl;

$R^9$, each time in which it occurs, is independently —OCF$_3$, halogen, —C(O)R$^{10}$, —C$_{1-6}$ alkyl, —N(R$^{12}$)$_2$, or —CF$_3$;

$R^{10}$ is a 6-membered heterocycle;

$R^{11}$, each time in which it occurs, is hydrogen or C$_{1-6}$ alkyl; and $R^{12}$, each time in which it occurs, is hydrogen or C$_{1-6}$ alkyl.

In one embodiment, $R^1$ is

In another embodiment, $R^1$ is

In another embodiment, $R^6$ is

In another embodiment, $R^6$ is

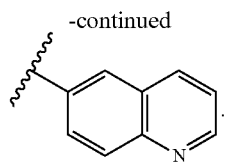

In another embodiment, $R^8$ is hydrogen, F or —CH$_3$. In a subclass of this embodiment, $R^8$ is F.

In another embodiment, $R^7$ is —C(NH)NH$_2$, —NH$_2$, —CN or —CH$_2$NH$_2$.

In another embodiment, $R^9$ is —OCF$_3$, F, —C(CH$_3$)$_3$, —CH$_2$CH$_3$, —CH$_3$, —N(CH$_3$)$_2$, —CF$_3$ or

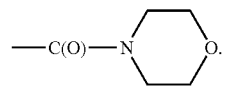

In another embodiment, the compound is
N-(4-carbamimidoylphenyl)-2-hydroxy-2-(4'-(trifluoromethoxy)biphenyl-3-yl)acetamide,
N-(4-carbamimidoylphenyl)-2-hydroxy-2-(4'-(trifluoromethoxy)biphenyl-3-yl)acetamide,
N-(3-aminobenzo[d]isoxazol-6-yl)-2-hydroxy-2-(4'-(trifluoromethoxy)biphenyl-3-yl)acetamide,
N-(3-aminobenzo[d]isoxazol-6-yl)-2-hydroxy-2-(4'-(trifluoromethoxy)biphenyl-3-yl)acetamide,
N-(1-aminoisoquinolin-6-yl)-2-hydroxy-2-(4'-(trifluoromethoxy)biphenyl-3-yl)acetamide,
N-(1-aminoisoquinolin-6-yl)-2-hydroxy-2-(4'-(trifluoromethoxy)biphenyl-3-yl)acetamide,
N-(4-carbamimidoylphenyl)-2-(4'-fluoro-3'-(morpholine-4-carbonyl)biphenyl-3-yl)-2-hydroxyacetamide hydrochloride,
N-(3-aminobenzo[d]isoxazol-6-yl)-2-(4'-fluoro-3'-(morpholine-4-carbonyl)biphenyl-3-yl)-2-hydroxyacetamide,
2-(4'-tert-butylbiphenyl-3-yl)-N-(4-carbamimidoylphenyl)-2-hydroxyacetamide hydrochloride,
N-(3-aminobenzo[d]isoxazol-6-yl)-2-(4'-tert-butylbiphenyl-3-yl)-2-hydroxyacetamide,
N-(1-aminoisoquinolin-6-yl)-2-(4'-tert-butylbiphenyl-3-yl)-2-hydroxyacetamide hydrochloride,
N-(2-aminoquinolin-6-yl)-2-(4'-tert-butylbiphenyl-3-yl)-2-hydroxyacetamide hydrochloride,
N-(4-(aminomethyl)phenyl)-2-(4'-tert-butylbiphenyl-3-yl)-2-hydroxyacetamide hydrochloride,
2-(4'-tert-butylbiphenyl-3-yl)-N-(2-cyanopyrimidin-5-yl)-2-hydroxyacetamide,
N-(1-aminoisoquinolin-6-yl)-2-(4'-ethylbiphenyl-3-yl)-2-hydroxyacetamide,
N-(1-aminoisoquinolin-6-yl)-2-[4'-(dimethylamino)biphenyl-3-yl]-2-hydroxyacetamide,
N-(1-aminoisoquinolin-6-yl)-2-(2'-ethylbiphenyl-3-yl)-2-hydroxyacetamide,
N-(1-aminoisoquinolin-6-yl)-2-hydroxy-2-[4'-(trifluoromethyl)biphenyl-3-yl]acetamide,
N-(1-aminoisoquinolin-6-yl)-2-hydroxy-2-{3-[6-(trifluoromethyl)pyridin-3-yl]phenyl}acetamide,
N-(1-aminoisoquinolin-6-yl)-2-(3'-ethylbiphenyl-3-yl)-2-hydroxyacetamide,
N-(3-amino-1,2-benzisoxazol-6-yl)-2-(4'-tert-butyl-2-fluorobiphenyl-3-yl)-2-hydroxyacetamide,
N-(3-amino-1,2-benzisoxazol-6-yl)-2-hydroxy-2-{6-[3-(trifluoromethyl)phenyl]pyridin-2-yl}acetamide,
N-(1-aminoisoquinolin-6-yl)-2-{3-[2-(dimethylamino)pyrimidin-5-yl]phenyl}-2-hydroxyacetamide,
N-(1-aminoisoquinolin-6-yl)-2-hydroxy-2-{3-[2-(trifluoromethyl)pyridin-4-yl]phenyl}acetamide,
N-[2-(aminomethyl)pyrimidin-5-yl]-2-(4'-tert-butylbiphenyl-3-yl)-2-hydroxyacetamide,
N-(3-amino-1,2-benzisoxazol-6-yl)-2-[6-(4-tert-butylphenyl)pyridin-2-yl]-2-hydroxyacetamide,
N-(1-aminoisoquinolin-6-yl)-2-(3',4'-dimethylbiphenyl-3-yl)-2-hydroxyacetamide,
N-(1-aminoisoquinolin-6-yl)-2-hydroxy-2-[3-(naphthalen-2-yl)phenyl]acetamide, or
N-(1-aminoisoquinolin-6-yl)-2-hydroxy-2-[3-(quinolin-6-yl)phenyl]acetamide.

Pharmaceutically acceptable salts include non-toxic salts such as those derived from inorganic acids, e.g. hydrochloric, hydrobromic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, carbonate, cyclopentanepropionate, digluconate, dodecylsulfate, ethanesulfonate, fumarate, glucoheptanoate, gluconate, glycerophosphate, hemisulfate, heptanoate, hexanoate, hippurate, hydrochloride, hydrobromide, hydroiodide, 2-hydroxyethanesulfonate, lactate, lactobionate, laurylsulfate, malate, maleate, mesylate, methanesulfonate, 2-naphthalenesulfonate, nicotinate, nitrate, oleate, oxalate, pamoate, pectinate, persulfate, 3-phenylpropionate, picrate, pivalate, propionate, stearate, succinate, sulfate, tartrate, thiocyanate, tosylate, and undecanoate. Additional specific anionic salts include ascorbate, gluceptate, glutamate, glucoronate, besylate, caprylate, isetionate, gentisate, malonate, napasylate, edfisylate, pamoate, xinafoate, and napadisylate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Additional specific cationic salts include tromethamine, benzathine, benethamine, diethylammonium, epolamine, hydrabamine.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof can form solvates with a solvent such as water, ethanol, or glycerol. The compounds of the present invention can form an acid addition salt and a salt with a base at the same time according to the type of substituent of the side chain.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

Some of the compounds described herein may exist as tautomers. The individual tautomers as well as mixtures thereof are encompassed with the described compounds.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or CH$_3$ or a symbol that is an extended bond as the terminal group, e.g. " 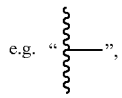 ", ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. C$_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, alkyl groups may be unsubstituted, or substituted with 1 to 3 substituents on any one or more carbon atoms, with halogen, C$_1$-C$_{20}$ alkyl, CF$_3$, NH$_2$, —NH(C$_1$-C$_6$ alkyl), —N(C$_1$-C$_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, C$_2$-C$_6$ alkynyl, (C$_1$-C$_6$ alkyl)S(O)$_{0-2}$—, HS(O)$_{0-2}$—, (C$_1$-C$_6$ alkyl)S(O)$_{0-2}$(C$_1$-C$_6$ alkyl)-, HS(O)$_{0-2}$(C$_1$-C$_6$ alkyl)-, (C$_0$-C$_6$ alkyl)C(O)NH—, H$_2$N—C(NH)—, —O(C$_1$-C$_6$ alkyl)CF$_3$, HC(O)—, (C$_1$-C$_6$ alkyl)C(O)—, HOC(O)—, (C$_1$-C$_6$ alkyl)OC(O)—, HO(C$_1$-C$_6$ alkyl)-, (C$_1$-C$_6$ alkyl)O(C$_1$-C$_6$ alkyl)-, (C$_1$-C$_6$ alkyl)C(O)$_{1-2}$(C$_1$-C$_6$ alkyl)-, HC(O)$_{1-2}$(C$_1$-C$_6$ alkyl)-, (C$_1$-C$_6$ alkyl)C(O)$_{1-2}$—, HOC(O)NH—, (C$_1$-C$_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, the term "aryl", alone or in combination, relates to a phenyl, naphthyl or indanyl group, preferably a phenyl group. The abbreviation "Ph" represents phenyl.

Except where noted herein, the term "heteroaryl" refers to a monocyclic unsaturated ring having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

The terms "heterocycle" and "heterocyclic" refer to a saturated monocyclic 5- to 8-membered ring having 1-4 heteroatoms selected from N, O and S, or a 7- to 12-membered saturated or partially saturated bicyclic ring system having 1-6 heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Except where noted herein, aryl groups may be unsubstituted, or substituted on any one or more carbon atoms, with halogen, C$_1$-C$_{20}$ alkyl, CF$_3$, NH$_2$, —NH(C$_1$-C$_6$ alkyl), —N(C$_1$-C$_6$ alkyl)$_2$, NO$_2$, oxo, CN, N$_3$, —OH, —O(C$_1$-C$_6$ alkyl), C$_3$-C$_{10}$ cycloalkyl, C$_2$-C$_6$ alkenyl, C$_2$-C$_6$ alkynyl, HS(O)$_{0-2}$—, (C$_1$-C$_6$ alkyl)S(O)$_{0-2}$—, (C$_1$-C$_6$ alkyl)S(O)$_{0-2}$ (C$_1$-C$_6$ alkyl)-, HS(O)$_{0-2}$(C$_1$-C$_6$ alkyl)-, (C$_1$-C$_6$ alkyl) S(O)$_{0-2}$, (C$_1$-C$_6$ alkyl)C(O)NH—, HC(O)NH—, H$_2$N—C (NH)—, —O(C$_1$-C$_6$ alkyl)CF$_3$, (C$_1$-C$_6$ alkyl)C(O)—, HC(O)—, (C$_1$-C$_6$ alkyl)OC(O)—, HOC(O)—, (C$_1$-C$_6$ alkyl) O(C$_1$-C$_6$ alkyl)-, HO(C$_1$-C$_6$ alkyl)-, (C$_1$-C$_6$ alkyl)C(O)$_{1-2}$ (C$_1$-C$_6$ alkyl)-, (C$_1$-C$_6$ alkyl)C(O)$_{1-2}$—, HC(O)$_{1-2}$(C$_1$-C$_6$ alkyl)-, (C$_1$-C$_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, the term "carbocycle" (and variations thereof such as "carbocyclic" or "carbocyclyl") as used herein, unless otherwise indicated, refers to a C$_3$ to C$_8$ monocyclic saturated or unsaturated ring. The carbocycle may be attached to the rest of the molecule at any carbon atom which results in a stable compound. Saturated carbocyclic rings are also referred to as cycloalkyl rings, e.g., cyclopropyl, cyclobutyl, etc.

Except where noted herein, heteroaryl and heterocyclic rings may be unsubstituted, or substituted on any one or more carbon atoms, with halogen, $C_1$-$C_{20}$ alkyl, $CF_3$, $NH_2$, —NH($C_1$-$C_6$ alkyl), —N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2N$—C(NH)—, —O($C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$, ($C_1$-$C_6$ alkyl)OC(O)NH—, HOC(O)NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_1$-$C_6$ alkyl, —C(O)$NH_2$, —$C_1$-$C_6$ alkylC(O)$NH_2$, —$C_1$-$C_6$ alkylOC(O)$NH_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound.

Except where noted herein, structures containing substituent variables such as variable "R" below:

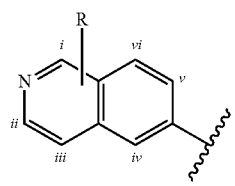

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

The invention also includes derivatives of the compound of Formula I, acting as prodrugs and solvates. Prodrugs, following administration to the patient, are converted in the body by normal metabolic or chemical processes, such as through hydrolysis in the blood, to the compound of Formula I. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments which contain an efficacious amount of at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

On account of their pharmacological properties, the compounds according to the invention are suitable, for example, for the prophylaxis, secondary prevention and therapy of all those diseases which are treatable by inhibition of blood clotting factor IXa. Thus, the compounds according to the invention are suitable as inhibitors both for prophylactic and for therapeutic administration to humans. They are suitable both for acute treatment and for long-term therapy. The compounds of the Formula (I) can be employed in patients who are suffering from disorders of well-being or diseases which accompany thromboses, embolisms, hypercoagulability or fibrotic changes.

These include myocardial infarct, angina pectoris and all other forms of acute coronary syndrome, stroke, peripheral vascular diseases, deep vein thrombosis, pulmonary embolism, embolic or thrombotic events caused by cardiac arrhythmias, cardiovascular events such as restenosis after revascularization, angioplasty and similar interventions such as stent implantations and bypass operations. Furthermore, the compounds of the Formula (I) can be employed in all interventions which lead to contact of the blood with foreign surfaces, as in dialysis patients and patients with indwelling catheters. Compounds of the Formula (I) can also be employed in order to reduce the risk of thrombosis after surgical interventions such as in knee and hip joint operations.

Compounds of the Formula (I) are suitable for the treatment of patients with disseminated intravascular coagulation, sepsis and other intravascular events which accompany inflammation. Furthermore, compounds of the Formula (I) are suitable for the prophylaxis and treatment of patients with atherosclerosis, diabetes and the metabolic syndrome and their sequelae. Disorders of the hemostatic system (for example fibrin deposits) have been implicated in mechanisms which lead to tumor growth and tumor metastasis, and in the inflammatory and degenerative joint diseases such as rheumatoid arthritis and arthrosis. Compounds of the Formula (I) are suitable for the retardation or prevention of such processes.

Further indications for the use of the compounds of the Formula (I) are fibrotic changes of the lungs such as chronic obstructive pulmonary disease, adult respiratory distress syndrome (ARDS) and of the eye, such as fibrin deposits after eye operations. Compounds of the Formula (I) are also suitable for the prevention and/or treatment of scar formation.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

Preferably, the pharmaceutical preparations are prepared and administered in dose units, where each unit contains as active constituent a certain dose of the compound of the Formula (I) according to the invention. In the case of solid dose units such as tablets, capsules, coated tablets or suppositories, this dose can be approximately 1000 mg, but preferably approximately 50 to 300 mg and in the case of injection solutions in ampoule form approximately 300 mg, but preferably approximately 10 to 100 mg.

For the treatment of an adult patient weighing approximately 70 kg, depending on the efficacy of the compound according to Formula (I), daily doses of approximately 2 mg to 1000 mg of active substance, preferably approximately 50 mg to 500 mg, are indicated. Under certain circumstances, however, higher or lower daily doses may also be appropriate. The daily dose can be administered both by single administration in the form of an individual dose unit or else of a number of smaller dose units and by multiple administration of subdivided doses at certain intervals.

Compounds of the Formula (I) can be administered both as a monotherapy and in combination with antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The effectiveness of compounds of the present invention to inhibit the coagulation factors XIa, VIIa, IXa, Xa, plasma kallikrein or thrombin, can be determined using a relevant purified serine protease, respectively, and an appropriate synthetic substrate.

Abbreviations
(Boc)$_2$O Di-tert-butyl dicarbonate
DIPA diisopropylamine
DMAP dimethylaminopyridine
EDCI 1-ethyl-3-(3-dimethylaminopropyl)carbodiimide
EtOAc ethyl acetate
EtOH ethanol
HCl hydrogen chloride
HPLC high performance liquid chromatography
LCMS Liquid Chromatography—Mass Spectrometry
MeOH methanol
Pd/C palladium on carbon
SFC supercritical fluid chromatography
TFA trifluoroacetic acid
THF tetrahydrofuran General Synthesis

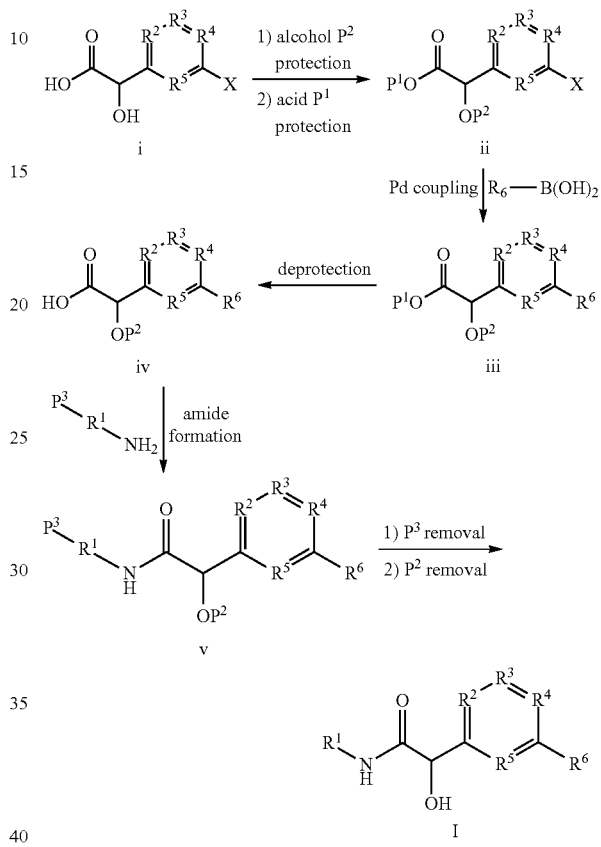

Above is a general synthetic scheme for compounds of Formula (I) starting from the α-hydroxy acid i. Standard protection of the alcohol with P$^2$ followed by standard acid protection with P$^1$ provides the doubly protected intermediate ii. Palladium coupling with an arylboronic acid R$^6$—B(OH)$_2$ yields the biaryl compound iii. Intermediate iv is generated from acid deprotection of compound iii. Activation of acid iv in the presence of amine P$^3$—R$^1$—NH$_2$ affords the protected amide v. Removal of the protecting groups P$^3$ and P$^2$ yields the final compound of Formula (I).

EXAMPLE 1

N-(4-carbamimidoylphenyl)-2-hydroxy-2-(4'-(trifluoromethoxy)biphenyl-3-yl)acetamide (Compound 9)

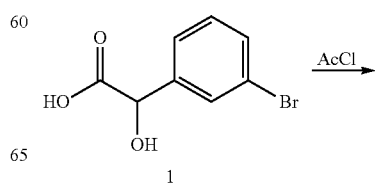

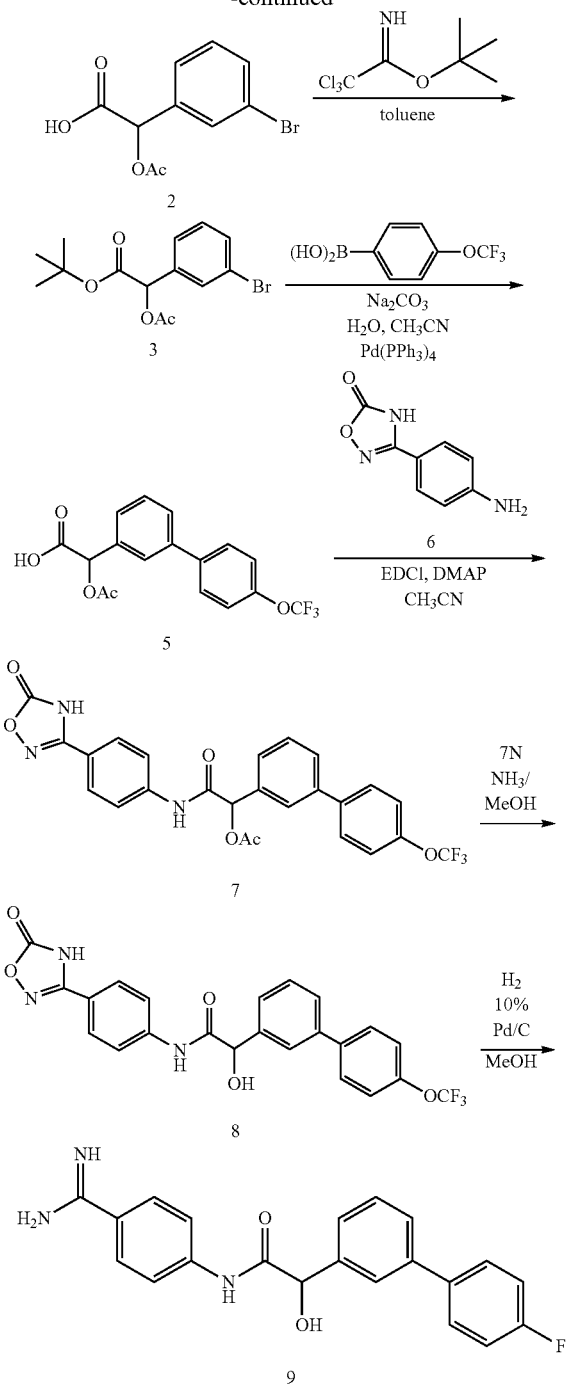

Synthesis of 2-acetoxy-2-(3-bromophenyl)acetic acid (compound 2)

Acetyl Chloride (1.5 mL) was added to 3-bromomandelic acid 1 (1.00 g, 4.33 mmol) and stirred at room temperature for 1 hour. The reaction mixture was concentrated in vacuo to provide compound 2 which was used in the next reaction without further purification.

Synthesis of tert-butyl 2-acetoxy-2-(3-bromophenyl)acetate (compound 3)

To a solution of compound 2 (500 mg, 1.83 mmol) in toluene (2.5 mL) was added t-butyl-trichloroacetimidate (0.33 mL). The reaction was stirred at room temperature for 5 hours. The solid precipitate was filtered off and washed with toluene. The filtrate was concentrated in vacuo to provide compound 3 which was used in the next reaction without further purification.

Synthesis of tert-butyl 2-acetoxy-2-(4'-(trifluoromethoxy)biphenyl-3-yl)acetate (compound 4)

A mixture of compound 3 (811 mg, 2.46 mmol), $Na_2CO_3$ (650 mg, 6.13 mmol), $Pd(PPh_3)_4$ (207 mg, 0.18 mmol) and 4-trifluoromethoxy phenyl boronic acid (870 mg, 4.22 mmol) in acetonitrile (7.0 mL) and water (0.7 mL) was heated to 130° C. in the microwave for 30 minutes. The mixture was filtered through Celite® diatomaceous earth and washed with EtOAc. The filtrate was concentrated in vacuo and the resulting residue was purified by flash chromatography (80 g silica cartridge, 0-10% EtOAc/hexanes) to provide compound 4.

Synthesis of 2-acetoxy-2-(4'-(trifluoromethoxy)biphenyl-3-yl)acetic acid (compound 5)

Compound 4 (100 mg, 0.24 mmol) was treated with TFA (0.6 mL) and water (20 µL) in $CH_2Cl_2$ (2 mL) at room temperature. After 4 hours, the reaction mixture was concentrated in vacuo to provide compound 5 which was used in the next reaction without further purification.

Synthesis of 2-oxo-2-(4-(5-oxo-4,5-dihydro-1,2,4-oxadiazol-3-yl)phenylamino)-1-(4'-(trifluoromethoxy)biphenyl-3-yl)ethyl acetate (compound 7)

Compound 5 (86 mg, 0.24 mmol) and 3-(4-aminophenyl)-1,2,4-oxadiazol-5(4H)-one 6 (44 mg, 0.5 mmol) were dissolved in $CH_3CN$ (2 mL) and cooled to 0° C. DMAP (8.5 mg, 0.07 mmol) and EDCI (96.7 mg, 0.5 mmol) were added to the reaction mixture and warmed to room temperature. After 3 hours, the mixture was diluted with EtOAc, washed with sat. $NH_4Cl$, dried over $MgSO_4$, filtered and concentrated in vacuo. The residue was purified by flash chromatography (24 g silica cartridge, 0-5% MeOH/$CH_2Cl_2$) to provide compound 7. LCMS M+23=536

Synthesis of 2-hydroxy-N-(4-(5-oxo-4,5-dihydro-1,2,4-oxadiazol-3-yl)phenyl)-2-(4'-(trifluoromethoxy)biphenyl-3-yl)acetamide (compound 8)

Compound 7 (71 mg, 0.14 mmol) was treated with 7N $NH_3$/MeOH (2 mL) and stirred at room temperature for 1.5 hours. The reaction was concentrated in vacuo to provide compound 8 which was used in the next reaction without further purification. LCMS M+23=472

Synthesis of N-(4-carbamimidoylphenyl)-2-hydroxy-2-(4'-(trifluoromethoxy)biphenyl-3-yl)acetamide (compound 9)

Compound 8 (10.4 mg, 0.022 mmol) was dissolved in MeOH (1 mL) and 3M HCl (0.2 mL). 10% Pd/C was added and the suspension was treated with a hydrogen balloon (1 atm.) for 3 hours. The solids were filtered through Celite® diatomaceous earth and washed with MeOH. The filtrate was concentrated in vacuo. The residue was purified by reverse phase HPLC to provide the desired product which was treated with HCl in ether to provide compound 9. LCMS M+H=430

EXAMPLES 2 AND 3

N-(4-carbamimidoylphenyl)-2-hydroxy-2-(4'-(trifluoromethoxy)biphenyl-3-yl)acetamide (enantiomer 1, compound 12) and N-(4-carbamimidoylphenyl)-2-hydroxy-2-(4'-(trifluoromethoxy)biphenyl-3-yl)acetamide (enantiomer 2, compound 13)

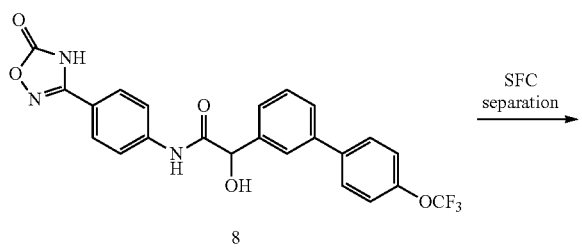

-continued

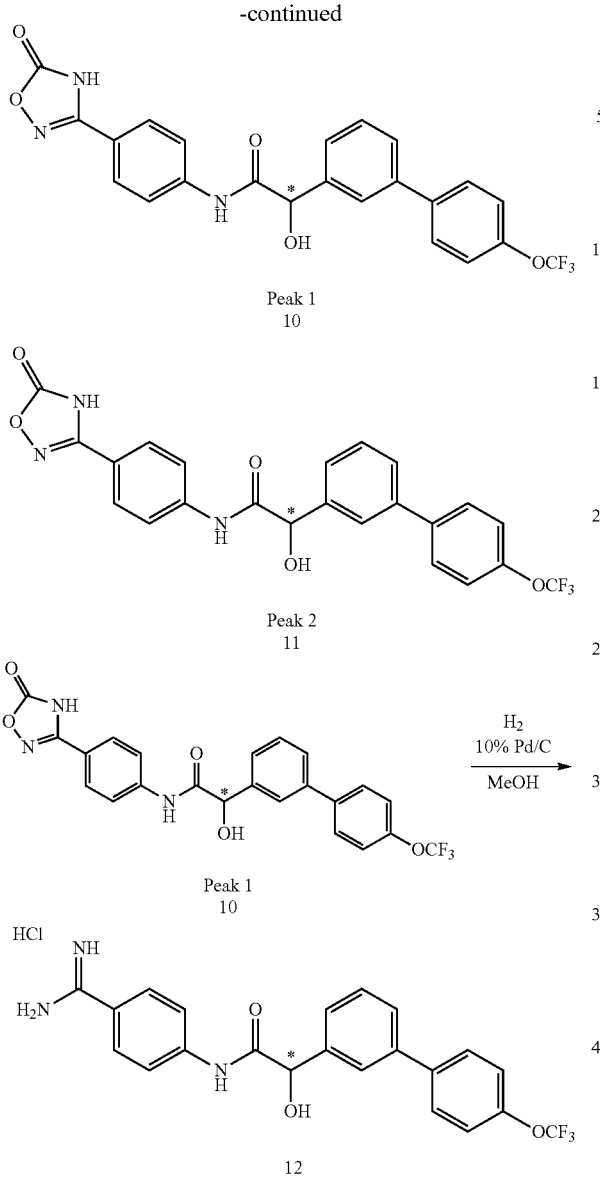

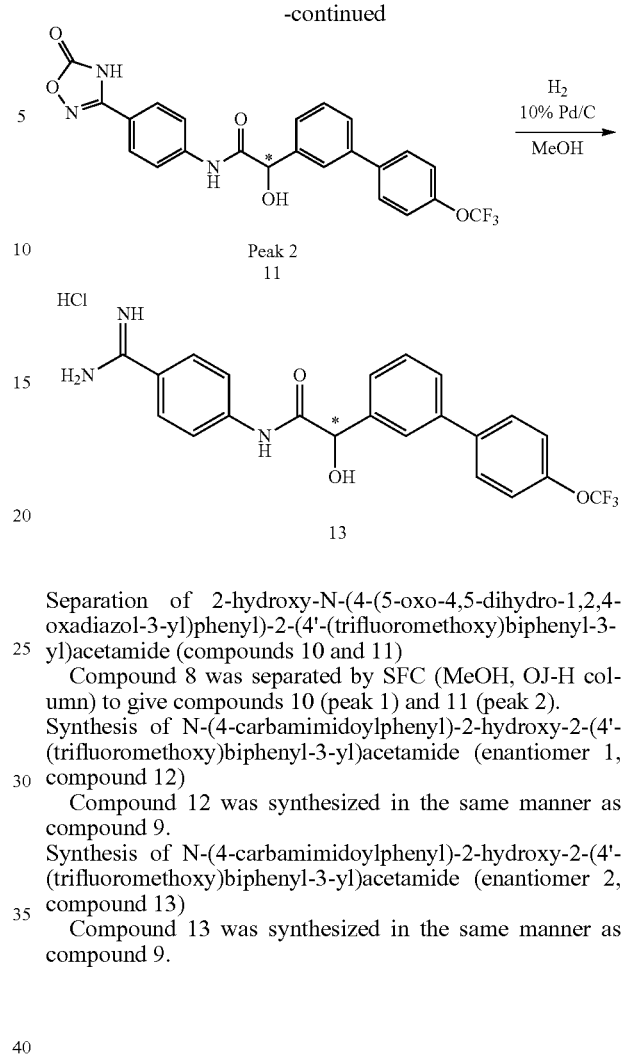

Separation of 2-hydroxy-N-(4-(5-oxo-4,5-dihydro-1,2,4-oxadiazol-3-yl)phenyl)-2-(4'-(trifluoromethoxy)biphenyl-3-yl)acetamide (compounds 10 and 11)

Compound 8 was separated by SFC (MeOH, OJ-H column) to give compounds 10 (peak 1) and 11 (peak 2).

Synthesis of N-(4-carbamimidoylphenyl)-2-hydroxy-2-(4'-(trifluoromethoxy)biphenyl-3-yl)acetamide (enantiomer 1, compound 12)

Compound 12 was synthesized in the same manner as compound 9.

Synthesis of N-(4-carbamimidoylphenyl)-2-hydroxy-2-(4'-(trifluoromethoxy)biphenyl-3-yl)acetamide (enantiomer 2, compound 13)

Compound 13 was synthesized in the same manner as compound 9.

EXAMPLE 4

N-(3-aminobenzo[d]isoxazol-6-yl)-2-hydroxy-2-(4'-(trifluoromethoxy)biphenyl-3-yl)acetamide (compound 16)

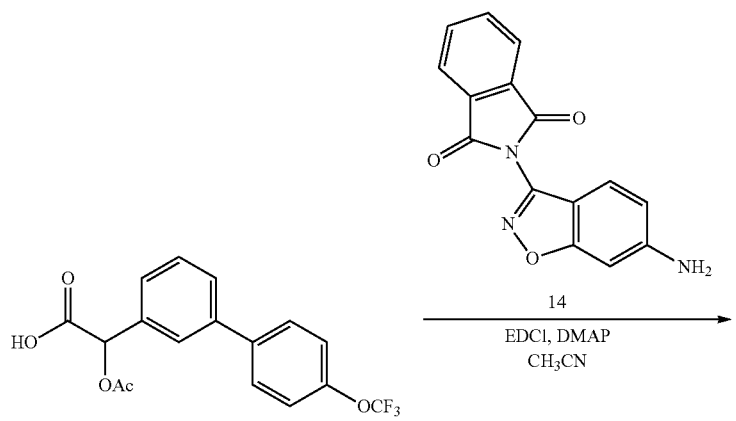

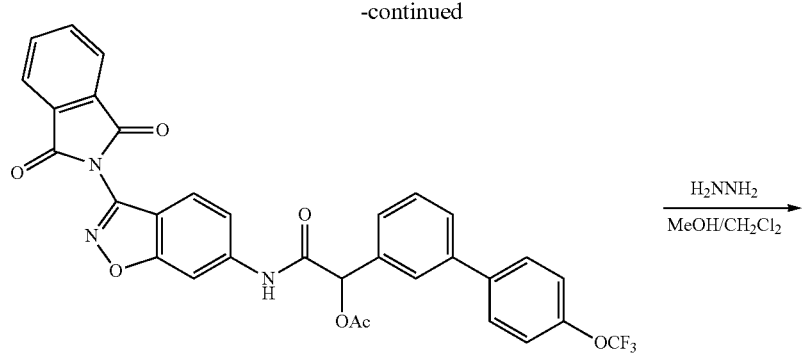

Synthesis of 2-(3-(1,3-dioxoisoindolin-2-yl)benzo[d]isoxazol-6-ylamino)-2-oxo-1-(4'-(trifluoromethoxy)biphenyl-3-yl)ethyl acetate (compound 15)

Compound 5 (251 mg, 0.71 mmol) and 2-(6-aminobenzo[d]isoxazol-3-yl)isoindoline-1,3-dione 14 (215 mg, 0.78 mmol) were dissolved in CH₃CN (3.5 mL) and cooled to 0° C. DMAP (12 mg, 0.1 mmol) and EDCI (160 mg, 0.83 mmol) were added to the mixture and stirred at room temperature overnight. The mixture was diluted with EtOAc, washed with sat. NH₄Cl, dried over MgSO₄, filtered and concentrated in vacuo. The residue was purified by flash chromatography (24 g silica cartridge, 0-5% acetone/hexanes) to provide a mixture 15 which was used in the next reaction without further purification.

Synthesis of N-(3-aminobenzo[d]isoxazol-6-yl)-2-hydroxy-2-(4'-(trifluoromethoxy)biphenyl-3-yl)acetamide (compound 16)

Compound 15 (141 mg, 0.023 mmol) was dissolved in a 1:1 mixture of CH₂Cl₂ and MeOH (10 mL) and hydrazine (0.07 mL) was added. The mixture was stirred at room temperature under nitrogen for 3 hours. The mixture was concentrated in vacuo. The residue was purified by preparative thin layer chromatography (5% MeOH/CH₂Cl₂) to provide compound 16. LCMS M+H=444

EXAMPLES 5 AND 6

N-(3-aminobenzo[d]isoxazol-6-yl)-2-hydroxy-2-(4'-(trifluoromethoxy)biphenyl-3-yl)acetamide (enantiomer 1, compound 17)

N-(3-aminobenzo[d]isoxazol-6-yl)-2-hydroxy-2-(4'-(trifluoromethoxy)biphenyl-3-yl)acetamide (enantiomer 2, compound 18)

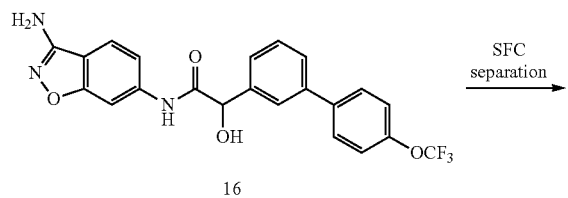

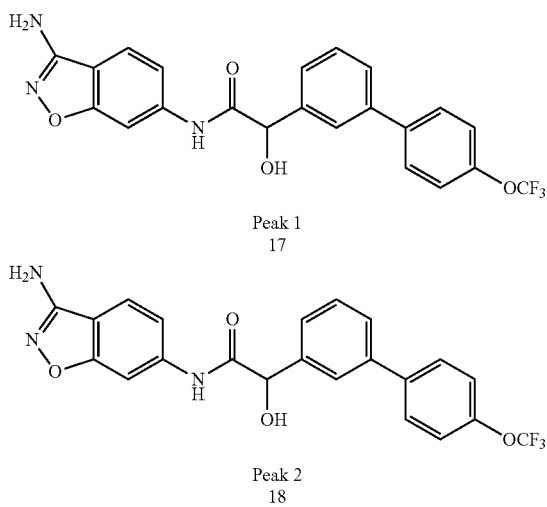

Separation of N-(3-aminobenzo[d]isoxazol-6-yl)-2-hydroxy-2-(4'-(trifluoromethoxy)biphenyl-3-yl)acetamide (compounds 17 and 18)

Compound 16 was separated by SFC (MeOH, 0.1% DIPA, OJ-H column) to give compound 17 (enantiomer 1) and compound 18 (enantiomer 2)

EXAMPLE 7

N-(1-aminoisoquinolin-6-yl)-2-hydroxy-2-(4'-(trifluoromethoxy)biphenyl-3-yl)acetamide (compound 22)

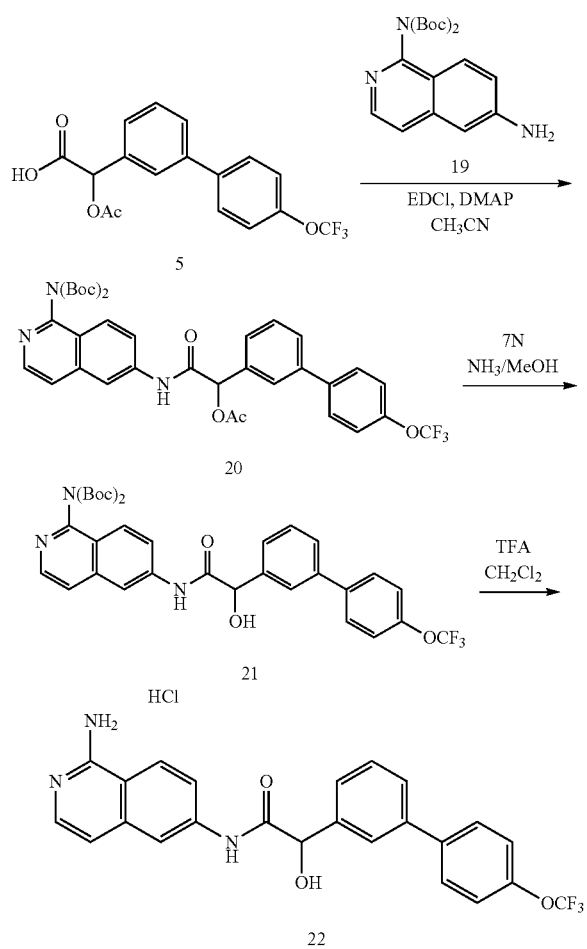

Synthesis of 2-(1-(bis(tert-butoxycarbonyl)amino)isoquinolin-6-ylamino)-2-oxo-1-(4'-(trifluoromethoxy)biphenyl-3-yl)ethyl acetate (compound 20)

Compound 5 (85 mg, 0.24 mmol) and compound 19 (100 mg, 0.28 mmol) were dissolved in $CH_2Cl_2$ (3.5 mL) and cooled to 0° C. DMAP (2.5 mg, 0.021 mmol) and EDCI (60 mg, 0.32 mmol) were added to the mixture and stirred at room temperature overnight. The mixture was diluted with $CH_2Cl_2$, washed with sat. $NH_4Cl$, dried over $MgSO_4$, filtered and concentrated in vacuo. The residue was purified by flash chromatography (24 g silica cartridge, 0-60% EtOAc/hexanes) to provide compound 20 (115 mg, 78%). LCMS: M+H=696

Synthesis of compound 21

Compound 20 (115 mg, 0.16 mmol) was treated with 7N $NH_3$/MeOH (3 mL) and stirred at room temperature for 1 hour. The reaction was concentrated in vacuo to provide compound 21 which was used in the next reaction without further purification. LCMS M+H=654

Synthesis of N-(1-aminoisoquinolin-6-yl)-2-hydroxy-2-(4'-(trifluoromethoxy)biphenyl-3-yl)acetamide (compound 22)

Compound 21 (97 mg, 0.16 mmol) was treated with TFA (1.0 mL) in $CH_2Cl_2$ (2.5 mL) at room temperature. After 35 minutes, the reaction mixture was concentrated in vacuo. The residue was treated with HCl in ether to provide compound 22. LCMS: M+H=454

EXAMPLES 8 AND 9

N-(1-aminoisoquinolin-6-yl)-2-hydroxy-2-(4'-(trifluoromethoxy)biphenyl-3-yl)acetamide (enantiomer 1, compound 23) and N-(1-aminoisoquinolin-6-yl)-2-hydroxy-2-(4'-(trifluoromethoxy)biphenyl-3-yl)acetamide (enantiomer 2, compound 24)

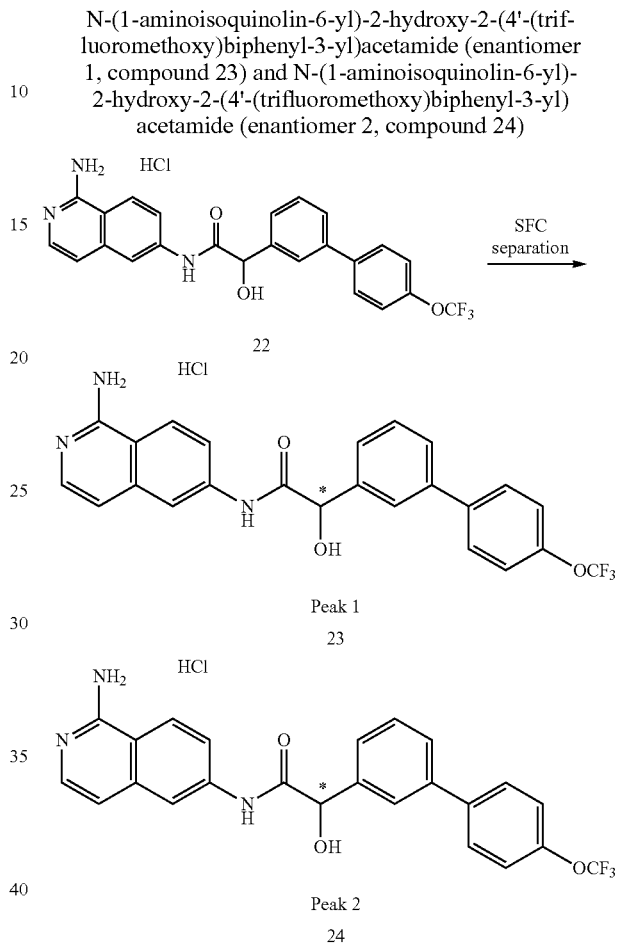

Separation of N-(1-aminoisoquinolin-6-yl)-2-hydroxy-2-(4'-(trifluoromethoxy)biphenyl-3-yl)acetamide (compounds 23 and 24)

Compound 22 was separated by SFC (1:1 EtOH/IPA, 0.1% DIPA, AD-H column) to give compound 23 (enantiomer 1) and compound 24 (enantiomer 2).

EXAMPLE 10

N-(4-carbamimidoylphenyl)-2-(4'-fluoro-3'-(morpholine-4-carbonyl)biphenyl-3-yl)-2-hydroxyacetamide hydrochloride (compound 30)

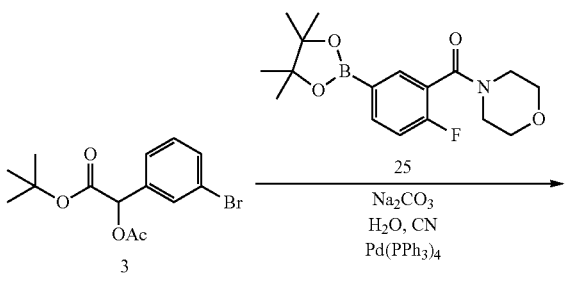

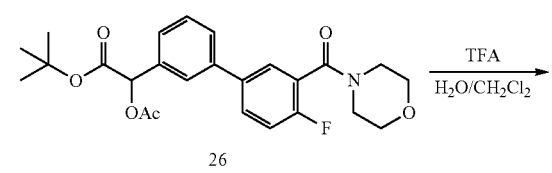
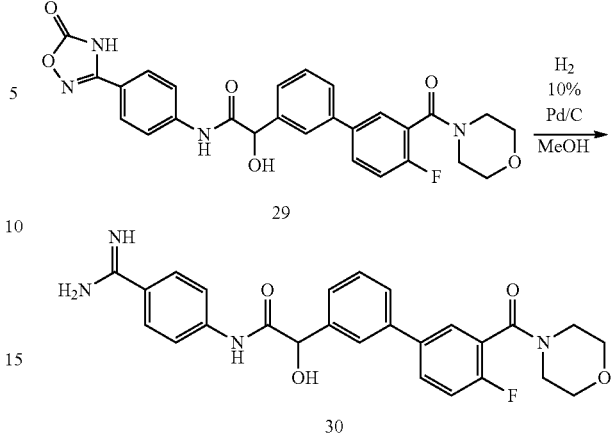
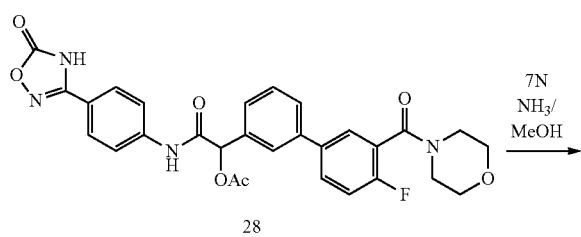
Synthesis of N-(4-carbamimidoylphenyl)-2-(4'-fluoro-3'-(morpholine-4-carbonyl)biphenyl-3-yl)-2-hydroxyacetamide hydrochloride (compound 30)
Compound 30 was synthesized in a similar manner to compound 9 by coupling compound 3 and the boronic ester 25.
EXAMPLE 11
N-(3-aminobenzo[d]isoxazol-6-yl)-2-(4'-fluoro-3'-(morpholine-4-carbonyl)biphenyl-3-yl)-2-hydroxy-acetamide (compound 32)
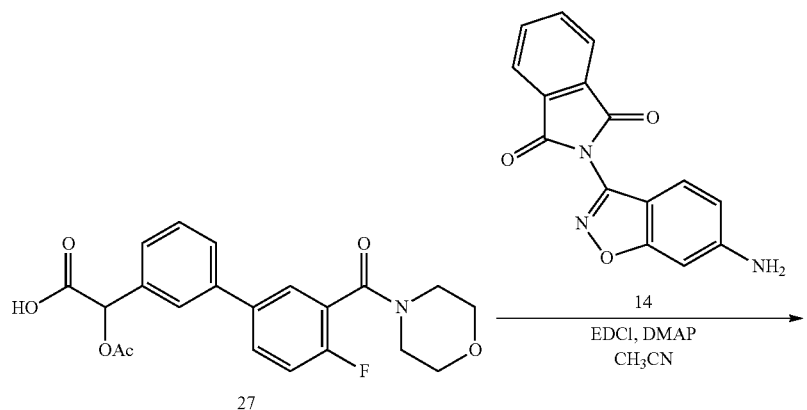
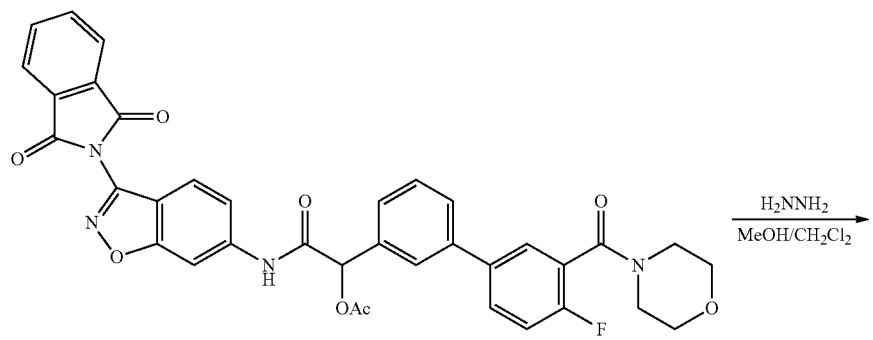

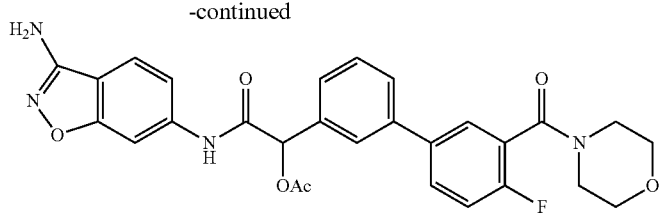
32
Synthesis of N-(3-aminobenzo[d]isoxazol-6-yl)-2-(4'-fluoro-3'-(morpholine-4-carbonyl)biphenyl-3-yl)-2-hydroxyacetamide (compound 32)
Compound 32 was synthesized in a similar manner to compound 9 by coupling compound 27 to compound 14.
EXAMPLE 12
2-(4'-tert-butylbiphenyl-3-yl)-N-(4-carbamimidoylphenyl)-2-hydroxyacetamide hydrochloride (compound 37)
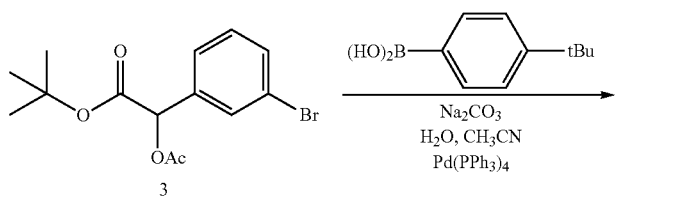
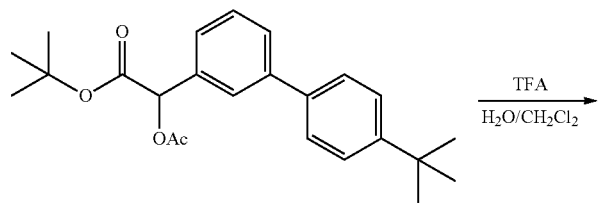
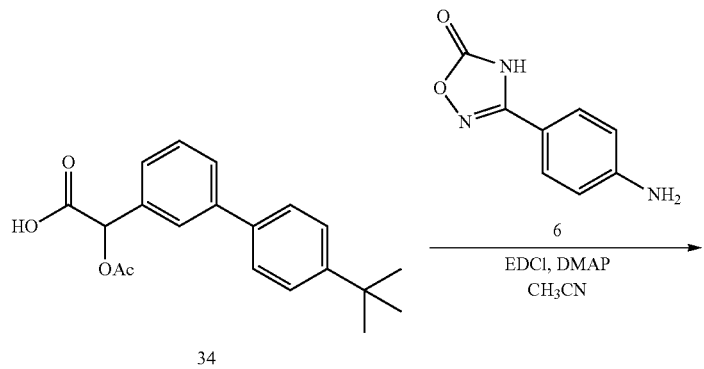
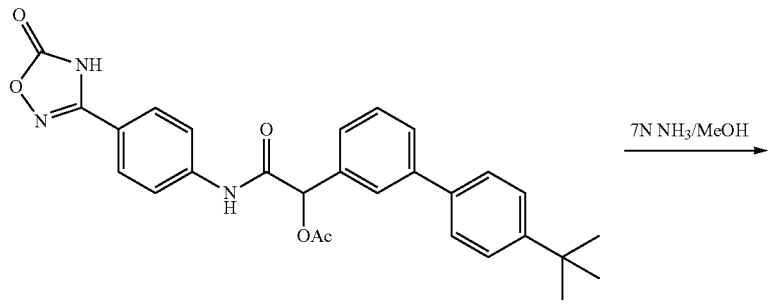

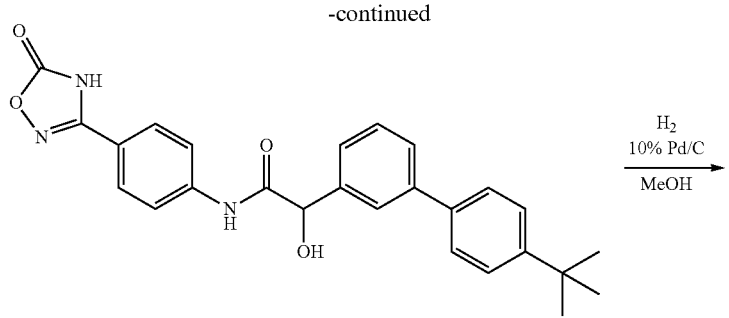

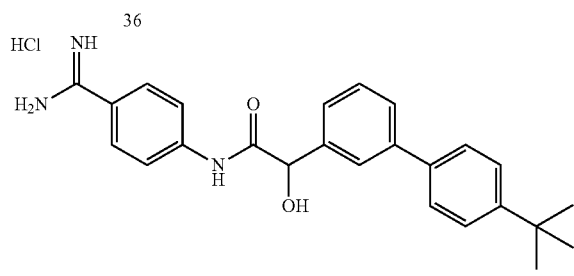

Synthesis of 2-(4'-tert-butylbiphenyl-3-yl)-N-(4-carbamimidoylphenyl)-2-hydroxyacetamide hydrochloride (compound 37)

Compound 37 was synthesized in the same manner as compound 9 by coupling compound 3 and 4-t-butyl phenylboronic acid.

EXAMPLE 13

N-(3-aminobenzo[d]isoxazol-6-yl)-2-(4'-tert-butylbiphenyl-3-yl)-2-hydroxyacetamide (compound 39)

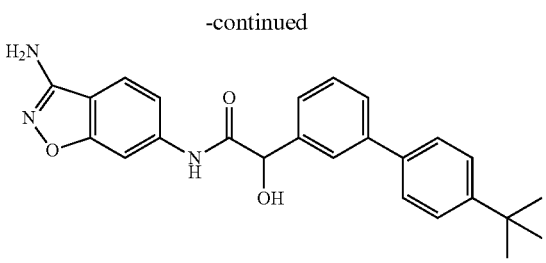

Synthesis of N-(3-aminobenzo[d]isoxazol-6-yl)-2-(4'-tert-butylbiphenyl-3-yl)-2-hydroxyacetamide (compound 39)

Compound 39 was synthesized in a similar manner to compound 16. M+H=416

EXAMPLE 14

N-(1-aminoisoquinolin-6-yl)-2-(4'-tert-butylbiphenyl-3-yl)-2-hydroxyacetamide hydrochloride (compound 42)

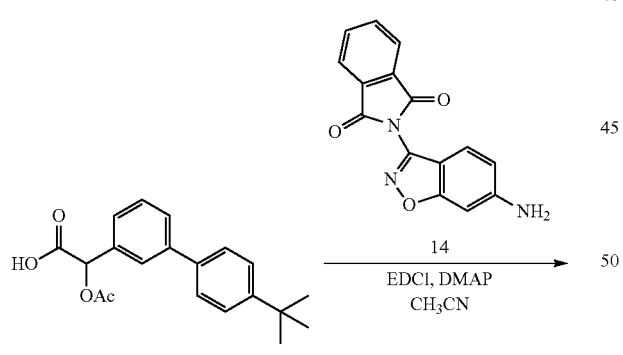

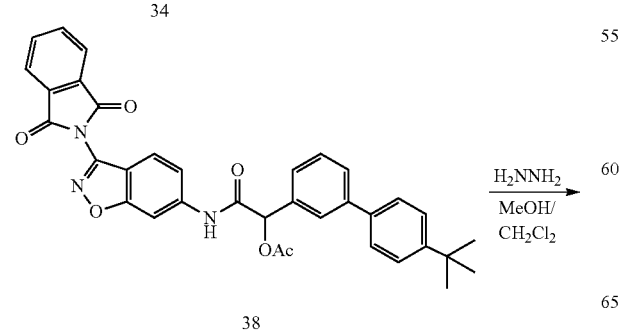

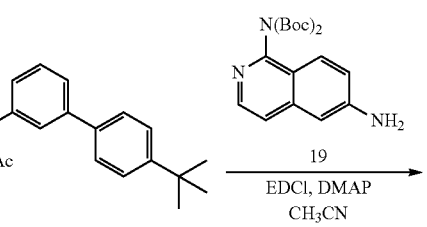

27
-continued
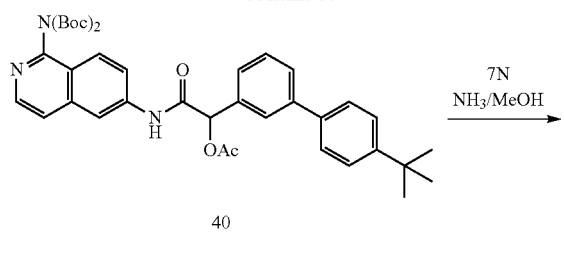
40
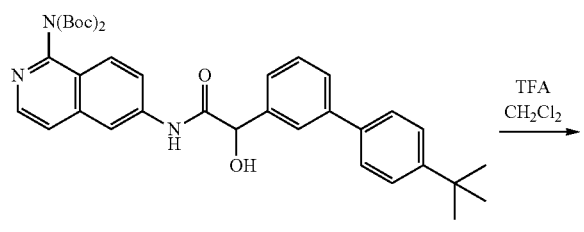
41
28
-continued
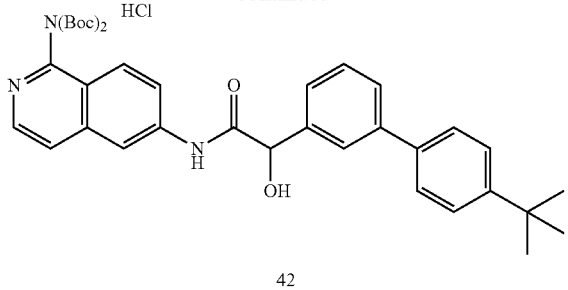
42
Synthesis of N-(1-aminoisoquinolin-6-yl)-2-(4'-tert-butylbiphenyl-3-yl)-2-hydroxyacetamide hydrochloride (compound 42)
Compound 42 was synthesized in the same manner as compound 22. M+H=426
EXAMPLE 15
N-(2-aminoquinolin-6-yl)-2-(4'-tert-butylbiphenyl-3-yl)-2-hydroxyacetamide hydrochloride (compound 48)
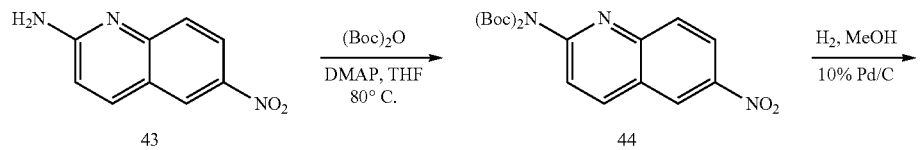
43      44
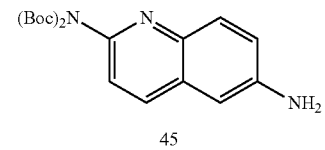
45
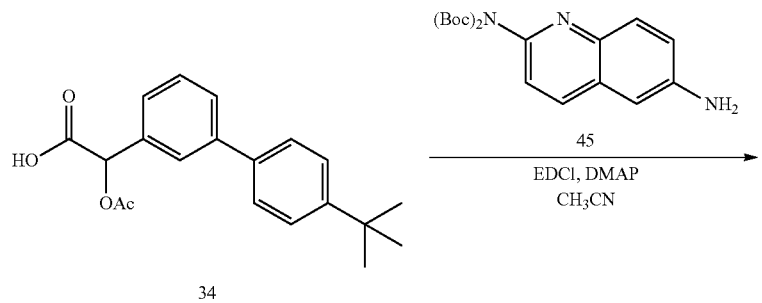
34
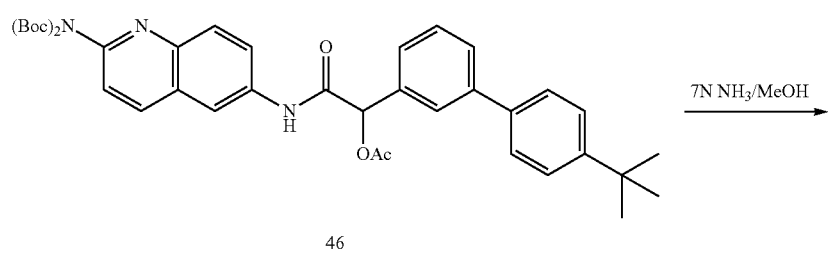
46

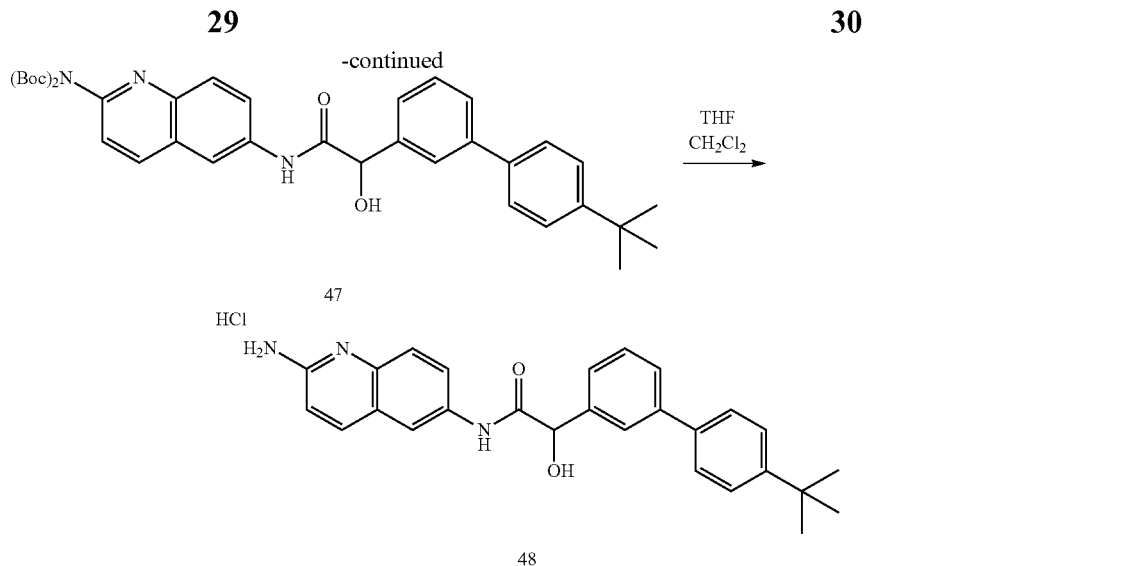

Synthesis of compound 44

To 6-nitroquinolin-2-amine 43 (1.0 g, 5.29 mmol) in THF (45 mL) was added (Boc)$_2$O (4.0 g, 18.4 mmol), followed by DMAP (102 mg, 0.836 mmol) at room temperature. The mixture was heated to reflux overnight. Additional (Boc)$_2$O (0.70 g, 3.21 mmol) and DMAP (60 mg, 0.49 mmol) were added to the reaction and refluxed overnight again. The reaction was cooled to room temperature and concentrated. The residue was taken up in CH$_2$Cl$_2$ and washed with saturated NH$_4$Cl, followed saturated NaHCO$_3$. The organics were dried over MgSO$_4$, filtered and concentrated in vacuo. The residue was purified by flash chromatography (120 g silica cartridge, 0-40% EtOAc/hexanes) to provide compound 44 (959 mg, 47%). M+23=412

Synthesis of compound 45

Compound 44 (958 mg, 2.46 mmol) was dissolved in MeOH (10 mL) and THF (10 mL). 10% Pd/C (58 mg) was added and the suspension was treated with a hydrogen balloon (1 atm) overnight. The solids were filtered through Celite®diatomaceous earth, washed with MeOH and THF. The filtrate was concentrated in vacuo to provide compound 46 (867 mg, 98%).

Synthesis of compound N-(2-aminoquinolin-6-yl)-2-(4'-tert-butylbiphenyl-3-yl)-2-hydroxyacetamide hydrochloride (compound 48)

Compound 48 was synthesized in the same manner as compound 22 by coupling compound 34 and compound 45.

EXAMPLE 16

N-(4-(aminomethyl)phenyl)-2-(4'-tert-butylbiphenyl-3-yl)-2-hydroxyacetamide hydrochloride (compound 52)

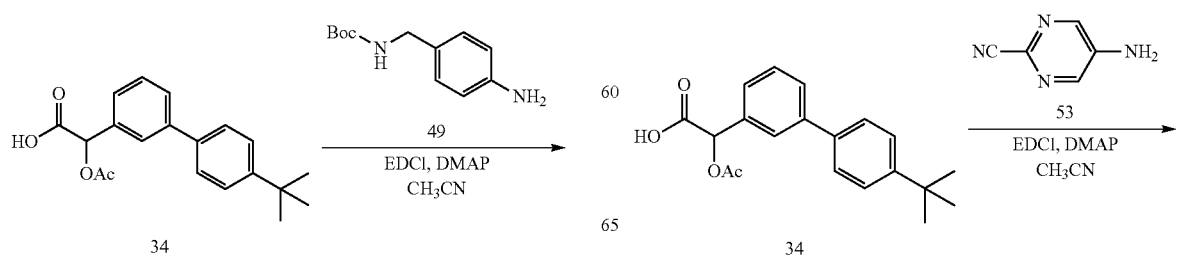

Synthesis of N-(4-(aminomethyl)phenyl)-2-(4'-tert-butylbiphenyl-3-yl)-2-hydroxyacetamide hydrochloride (compound 52)

Compound 52 was synthesized in the same manner as compound 22 by coupling compound 34 and compound 49.

EXAMPLE 17

2-(4'-tert-butylbiphenyl-3-yl)-N-(2-cyanopyrimidin-5-yl)-2-hydroxyacetamide (compound 55)

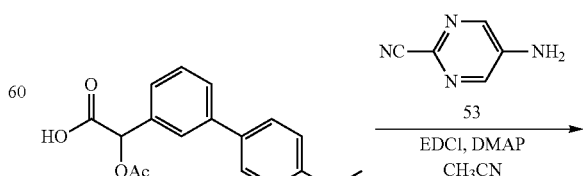

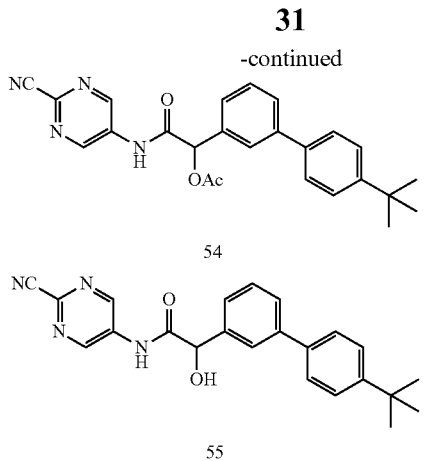

Synthesis of 2-(4'-tert-butylbiphenyl-3-yl)-N-(2-cyanopyrimidin-5-yl)-2-hydroxyacetamide (compound 55)

Compound 55 was synthesized in the same manner as compound 8 by coupling compound 34 and compound 53.

TABLE 1

| Compound | LCMS | ¹H NMR |
|---|---|---|
| 9 | M + H = 430 | ¹H NMR (400 MHz, METHANOL-$d_4$) δ ppm 5.28 (s, 1 H) 7.35 (d, J = 8.07 Hz, 2 H) 7.43-7.51 (m, 1 H) 7.58 (dd, J = 14.31, 7.70 Hz, 2 H) 7.70-7.80 (m, 4 H) 7.82 (s, 1 H) 7.92 (dd, J = 8.80, 1.28 Hz, 2 H) |
| 12 | M + H = 430 | ¹H NMR (400 MHz, METHANOL-$d_4$) δ ppm 5.28 (s, 1 H) 7.35 (d, J = 8.07 Hz, 2 H) 7.42-7.51 (m, 1 H) 7.58 (dd, J = 14.40, 7.61 Hz, 2 H) 7.67-7.86 (m, 5 H) 7.93 (d, J = 8.80 Hz, 2 H) |
| 13 | M + H = 430 | ¹H NMR (400 MHz, METHANOL-$d_4$) δ ppm 5.28 (s, 1 H) 7.35 (d, J = 8.25 Hz, 2 H) 7.43-7.51 (m, 1 H) 7.58 (dd, J = 14.12, 7.70 Hz, 2 H) 7.68-7.85 (m, 5 H) 7.93 (d, J = 8.80 Hz, 2 H) |
| 16 | M + H = 444 | ¹H NMR (400 MHz, METHANOL-$d_4$) δ ppm 5.27 (s, 1 H) 7.31-7.43 (m, 3 H) 7.44-7.51 (m, 1 H) 7.54-7.62 (m, 2 H) 7.66 (d, J = 8.44 Hz, 1 H) 7.70-7.77 (m, 2 H) 7.83 (s, 1 H) 7.92 (d, J = 1.28 Hz, 1 H) |
| 17 | M + H = 444 | ¹H NMR (400 MHz, METHANOL-$d_4$) δ ppm 5.27 (s, 1 H) 7.31-7.43 (m, 3 H) 7.44-7.52 (m, 1 H) 7.54-7.62 (m, 2 H) 7.66 (d, J = 8.62 Hz, 1 H) 7.73 (d, J = 8.80 Hz, 2 H) 7.83 (s, 1 H) 7.92 (d, J = 1.28 Hz, 1 H) |
| 18 | M + H = 444 | ¹H NMR (400 MHz, METHANOL-$d_4$) δ ppm 5.27 (s, 1 H) 7.35 (d, J = 8.25 Hz, 2 H) 7.41 (dd, J = 8.53, 1.56 Hz, 1 H) 7.44-7.51 (m, 1 H) 7.54-7.62 (m, 2 H) 7.66 (d, J = 8.62 Hz, 1 H) 7.73 (d, J = 8.80 Hz, 2 H) 7.83 (s, 1 H) 7.92 (d, J = 1.10 Hz, 1 H) |
| 22 | M + H = 454 | ¹H NMR (400 MHz, METHANOL-$d_4$) δ ppm 5.33 (s, 2 H) 7.12 (d, J = 6.97 Hz, 1 H) 7.35 (d, J = 8.25 Hz, 2 H) 7.45-7.52 (m, 2 H) 7.56-7.64 (m, 2 H) 7.70-7.76 (m, 2 H) 7.85 (s, 1 H) 8.00 (dd, J = 9.08, 2.11 Hz, 1 H) 8.32-8.40 (m, 2 H) |
| 23 | M + H = 454 | ¹H NMR (400 MHz, METHANOL-$d_4$) δ ppm 5.33 (s, 1 H) 7.12 (d, J = 7.15 Hz, 1 H) 7.35 (d, J = 8.25 Hz, 2 H) 7.42-7.52 (m, 2 H) 7.55-7.64 (m, 2 H) 7.73 (d, J = 8.62 Hz, 2 H) 7.84 (s, 1 H) 8.00 (dd, J = 8.99, 2.02 Hz, 1 H) 8.30-8.41 (m, 2 H) |
| 24 | M + H = 454 | ¹H NMR (400 MHz, METHANOL-$d_4$) δ ppm 5.32 (s, 1 H) 7.12 (d, J = 7.15 Hz, 1 H) 7.35 (d, J = 8.07 Hz, 2 H) 7.45-7.52 (m, 2 H) 7.54-7.64 (m, 2 H) 7.73 (d, J = 8.80 Hz, 2 H) 7.84 (s, 1 H) 8.00 (dd, J = 9.08, 1.74 Hz, 1 H) 8.31-8.40 (m, 2 H) |
| 30 | M + H = 477 | ¹H NMR (400 MHz, METHANOL-$d_4$) δ ppm 3.40 (br. s., 2 H) 3.64 (t, J = 4.68 Hz, 2 H) 3.72-3.84 (m, 4 H) 5.27 (s, 1 H) 7.30 (t, J = 8.99 Hz, 1 H) 7.42-7.51 (m, 1 H) 7.54-7.62 (m, 2 H) 7.67 (dd, J = 6.24, 2.38 Hz, 1 H) 7.73-7.82 (m, 4 H) 7.92 (d, J = 8.80 Hz, 2 H) 8.64 (br. s., 1 H) 9.16 (br. s., 1 H) |
| 32 | M + H = 491 | ¹H NMR (400 MHz, METHANOL-$d_4$) δ ppm 3.40 (br. s., 2 H) 3.63 (t, J = 4.68 Hz, 2 H) 3.78 (dd, J = 13.94, 4.59 Hz, 4 H) 5.26 (s, 1 H) 7.30 (t, J = 8.99 Hz, 1 H) 7.40 (dd, J = 8.53, 1.56 Hz, 1 H) 7.43-7.51 (m, 1 H) 7.54-7.62 (m, 2 H) 7.63-7.71 (m, 2 H) 7.74-7.84 (m, 2 H) 7.91 (d, J = 1.10 Hz, 1 H) |
| 37 | M + H = 402 | ¹H NMR (400 MHz, METHANOL-$d_4$) δ ppm 1.35 (s, 9 H) 5.26 (s, 1 H) 7.40-7.52 (m, 4 H) 7.53-7.61 (m, 3 H) 7.73-7.82 (m, 3 H) 7.91 (s, 2 H) |
| 39 | M + H = 416 | ¹H NMR (400 MHz, METHANOL-$d_4$) δ ppm 1.34 (s, 9 H) 5.26 (s, 1 H) 7.36-7.53 (m, 5 H) 7.57 (d, J = 8.62 Hz, 3 H) 7.65 (s, 1 H) 7.81 (s, 1 H) 7.92 (d, J = 1.28 Hz, 1 H) |
| 42 | M + H = 426 | ¹H NMR (400 MHz, METHANOL-$d_4$) δ ppm 1.34 (s, 9 H) 5.31 (s, 1 H) 7.08-7.16 (m, 1 H) 7.40-7.61 (m, 8 H) 7.82 (s, 1 H) 7.95-8.03 (m, 1 H) 8.34 (d, J = 1.65 Hz, 1 H) |
| 48 | M + H = 426 | ¹H NMR (400 MHz, METHANOL-$d_4$) δ ppm 1.35 (s, 9 H) 5.27 (s, 1 H) 7.04 (d, J = 9.54 Hz, 1 H) 7.39-7.64 (m, 8 H) 7.81 (s, 1 H) 7.93-8.02 (m, 1 H) 8.28 (d, J = 3.12 Hz, 1 H) |
| 52 | M + H = 389 | ¹H NMR (400 MHz, METHANOL-$d_4$) δ ppm 1.35 (s, 9 H) 4.06 (s, 2 H) 5.23 (s, 1 H) 7.36-7.52 (m, 6 H) 7.53-7.60 (m, 3 H) 7.71 (d, J = 8.44 Hz, 2 H) 7.78 (s, 1H) |
| 55 | M + H = 387 | ¹H NMR (400 MHz, CHLOROFORM-d) δ ppm 1.36 (s, 9 H) 3.42-3.55 (m, 1 H) 5.38 (s, 1 H) 7.40-7.55 (m, 6 H) 7.58-7.64 (m, 1 H) 7.68 (s, 1 H) 8.90-8.96 (m, 1 H) 9.14 (s, 2 H) |

The following additional exemplary compounds may be prepared according to procedures similar to those described above.

TABLE 2

| Structure | Name/LCMS |
|---|---|
| 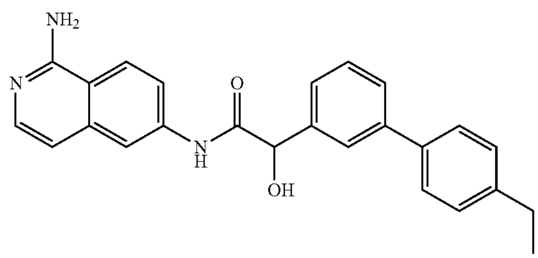 [SMILES: CCc1ccc(-c2cccc(C(O)C(=O)Nc3ccc4c(N)nccc4c3)c2)cc1] | N-(1-aminoisoquinolin-6-yl)-2-(4'-ethylbiphenyl-3-yl)-2-hydroxyacetamide<br>M + H = 398 |

TABLE 2-continued

| Structure | Name/LCMS |
|---|---|
| | N-(1-aminoisoquinolin-6-yl)-2-[4'-(dimethylamino)biphenyl-3-yl]-2-hydroxyacetamide<br>M + H = 413 |
| | N-(1-aminoisoquinolin-6-yl)-2-(2'-ethylbiphenyl-3-yl)-2-hydroxyacetamide<br>M + H = 398 |
| | N-(1-aminoisoquinolin-6-yl)-2-hydroxy-2-[4'-(trifluoromethyl)biphenyl-3-yl]acetamide<br>M + H = 438 |
| | N-(1-aminoisoquinolin-6-yl)-2-hydroxy-2-{3-[6-(trifluoromethyl)pyridin-3-yl]phenyl}acetamide<br>M + H = 439 |
| | N-(1-aminoisoquinolin-6-yl)-2-(3'-ethylbiphenyl-3-yl)-2-hydroxyacetamide<br>M + H = 398 |
| | N-(3-amino-1,2-benzisoxazol-6-yl)-2-(4'-tert-butyl-2-fluorobiphenyl-3-yl)-2-hydroxyacetamide |

TABLE 2-continued

| Structure | Name/LCMS |
|---|---|
| | N-(3-amino-1,2-benzisoxazol-6-yl)-2-hydroxy-2-{6-[3-(trifluoromethyl)phenyl]pyridin-2-yl}acetamide |
| | N-(1-aminoisoquinolin-6-yl)-2-{3-[2-(dimethylamino)pyrimidin-5-yl]phenyl}-2-hydroxyacetamide<br>M + H = 415 |
| | N-(1-aminoisoquinolin-6-yl)-2-hydroxy-2-{3-[2-(trifluoromethyl)pyridin-4-yl]phenyl}acetamide<br>M + H = 439 |
| | N-[2-(aminomethyl)pyrimidin-5-yl]-2-(4'-tert-butylbiphenyl-3-yl)-2-hydroxyacetamide<br>M + H = 391 |
| | N-(3-amino-1,2-benzisoxazol-6-yl)-2-[6-(4-tert-butylphenyl)pyridin-2-yl]-2-hydroxyacetamide |
| | N-(1-aminoisoquinolin-6-yl)-2-(3',4'-dimethylbiphenyl-3-yl)-2-hydroxyacetamide<br>M + H = 398 |

TABLE 2-continued

| Structure | Name/LCMS |
|---|---|
| [structure of N-(1-aminoisoquinolin-6-yl)-2-hydroxy-2-[3-(naphthalen-2-yl)phenyl]acetamide] | N-(1-aminoisoquinolin-6-yl)-2-hydroxy-2-[3-(naphthalen-2-yl)phenyl]acetamide<br>M + H = 420 |
| [structure of N-(1-aminoisoquinolin-6-yl)-2-hydroxy-2-[3-(quinolin-6-yl)phenyl]acetamide] | N-(1-aminoisoquinolin-6-yl)-2-hydroxy-2-[3-(quinolin-6-yl)phenyl]acetamide<br>M + H = 421 |

Determination of Inhibitory Activity Against Factor IXa

Inhibitory activity against factor IXa was tested using the substrate SPECTROFLUOR FIXa (American Diagnostica Inc.; 500 West Avenue, Stamford, Conn. 06902 USA; Pr. No. 299F) and human factor IXa (American Diagnostica Inc.; Pr. No. 449b). Test substances dissolved in buffer A (50 mM α,α,α-tris (hydroxymethyl)methylamine (Tris), 100 mM NaCl, 5 mM CaCl$_2$, 15% (v/v) ethylene glycol, pH 8.0) were mixed with factor IXa (2.0 µg/ml final concentration). The enzyme reaction was started by addition of SPECTROFLUOR FIXa (100 µM final concentration). After incubation for 60 minutes at room temperature, the reaction was stopped by the addition of 20% (v/v) acetic acid solution, and then fluorescence value measured (Excitation Wavelength:355 nm, Emission Wavelength; 460 nm) in a microtiter plate reader (ARVO 1420 Multilabel Counter; PerkinElmer).

IC$_{50}$ was calculated from a dilution series of the test substance with the aid of the software, Symix Assay Explorer (Symyx Technologies, Inc.). Table 3 shows the results.

TABLE 3

| Compound | Factor IXa enzyme assay IC$_{50}$ [nM] |
|---|---|
| 9 | 440 |
| 13 | 450 |
| 22 | 760 |
| 37 | 160 |
| 42 | 695 |
| 52 | 1450 |

Determination of Inhibitory Activity Against Factor Xa

Inhibitory activity against factor Xa is tested using the substrate SPECTROFLUOR FXa (American Diagnostica Inc.; 500 West Avenue, Stamford, Conn. 06902 USA; Pr. No. 222F) and human factor Xa (American Diagnostica Inc.; Pr. No. 526). Test substances dissolved in buffer B (20 mM Tris, 200 mM NaCl, 2.5 mM CaCl$_2$, pH 8.0) are mixed with factor Xa (44 ng/ml final concentration). The enzyme reaction is started by addition of SPECTROFLUOR FXa (100 µM final concentration). After incubation for 60 minutes at room temperature, the reaction is stopped by the addition of 20% (v/v) acetic acid solution, and then fluorescence value measured (Excitation Wavelength:355 nm, Emission Wavelength; 460 nm) in a microtiter plate reader (ARVO 1420 Multilabel Counter; PerkinElmer).

Selectivity Calculation

Selectivity for Factor IXa activity over Factor Xa activity can be determined by the following calculation: (IC50 Factor Xa)/(IC50 Factor IXa). Similar calculations can be made for selectivity of compounds for Factor IXa compared to other coagulation factors. These as well as other ways of minimizing contact between the components of combination products of the present invention, whether administered in a single dosage form or administered in separate forms but at the same time by the same manner, will be readily apparent to those skilled in the art, once armed with the present disclosure.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

Because of their inhibitory action, these compounds are indicated for use in the prevention or treatment of physiological reactions, conditions including thromboembolic disorder (arterial cardiovascular thromboembolic disorders, venous cardiovascular thromboembolic disorders, thromboembolic disorders in the chambers of the heart, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis), blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents anti-platelet or platelet inhibitory agents, anti-inflammatory agents, thrombin inhibitors, thrombolytic or fibrinolytic agents, thrombin receptor (PAR-1) antagonists, factor VIIa inhibitors, factor VIIIa inhibitor, factor IXa inhibitors different from the compound of claim 1, factor Xa inhibitors, factor XIa inhibitors, TAFIs, and fibrinogen inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVANO), aprotinin, synthetic pentasaccharide, direct acting thrombin inhibitors including hirudin, dabigatran and argatroban, as well as other factor VIIa inhibitors, VIIIa inhibitors, IXa inhibitors, Xa inhibitors, XIa inhibitors, thrombin inhibitors, fibrinogen inhibitors, TAFI, and others known in the art. Factor IXa inhibitors different from the compounds of Formula (I) include synthetic active-site blocked competitive inhibitors, oral inhibitors and RNA aptamers. These are described in the previously cited Howard et al. reference (Howard, E L, Becker K C, Rusconi, C P, Becker R C. Factor IXa Inhibitors as Novel Anticoagulents. *Arterioscler Thromb Vasc Biol.* 2007; 27: 722-727.).

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferable antagonists of the purinergic receptors P2Y1 and P2Y12 with P2Y12 being even more preferred. Preferred P2Y12 receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, dabigatran and argatroban, including pharmaceutically acceptable salts and prodrugs thereof. Boroarginine derivatives and boropeptiders include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J. Med. Chem.*, vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-NH2 and N-trans-cinnamoyl-p-fluoroPhe-p-guanidinoPhe-Leu-Arg-Arg-NH2. Peptide thrombin receptor antagonists are also disclosed in WO 94/03479.

Substituted tricyclic thrombin receptor antagonists are disclosed in U.S. Pat. Nos. 6,063,847, 6,326,380 and WO 01/96330 and Ser. No. 10/271,715.

Other thrombin receptor antagonists include those disclosed in U.S. Pat. Nos. 7,1304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PM-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complexes, as described, for example, in European Patent Application No. 028,489. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvedilol and propranolol); Class III agents (such as sotalol, dofetilide, aminodarone, azimilide and ibutilide); Class IV agents (such as ditiazem and verapamil); IAch inhibitors, and IKur inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamil nifedipine, amlodipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamterene, amiloride, spironolactone); renin inhibitors; angiotensin-converting enzyme (ACE) inhibitors (e.g., captopril, Lisinopril, fosinopril, enalapril, ceranopril, cilazopril, delapril, pentopril, quinapril, ramipril, Lisinopril); angiotensin-II-receptor antagonists (e.g., irbestatin, Losartan, valsartan); ET receptor antagonists (e.g., sitaxsentan, atrsentan and compounds disclosed in U.S. Pat. Nos. 5,612, 359 and 6,043,265); Dual ET/All antagonist (e.g., compounds disclosed in WO 00/01389); neutral endopeptidase (NEP) inhibitors; vasopepsidase inhibitors (dual CCE/NEP inhibitors, e.g., omapatrilat, gemopatrilat, nitrates); and β-blockers (e.g., propranolol, nadolol, or carvedilol).

Examples of suitable cardiac glycosides for use in combination with compounds of the present invention include digitalis and ouabain. Examples of suitable mineralocorticoid receptor antagonists for use in combination with the compounds of the present invention include spironolactone and eplirinone. Examples of suitable cholesterol/lipid lowering agents and lipid profile therapies for use in combination with the compounds of the present invention include: HMG-CoA reductase inhibitors (e.g., pravastatin, lovastatin, atrbastatin, simvastatin, fluvastatin, NK-104 (itavastatin, or nisvastatin or nisbastatin) and ZD-4522 (rosuvastatin, or atavastatin or visastatin); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414). Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors, including sitagliptin. Examples of suitable anti-depressant agents for use in combination with compounds of the present invention include nefazodone and sertraline. Examples of suitable anti-inflammatory agents for use in combination with compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; piroxicam; naproxen; celecoxib; and/or rofecoxib. Examples of suitable anti-osteoporosis agents for use in combination with the compounds of the present invention include alendronate and raloxifene. Examples of suitable hormone replacement therapies for use in combination with the compounds of the present invention include estrogen (e.g., conjugated estrogens) and estradiol. Examples of suitable anti-obesity agents for use in combination with the compounds of the present invention include orlistat and a P2 inhibitor (such as those disclosed in WO00/59506). Examples of suitable anti-anxiety agents for use in combination with the compounds of the present invention include diazepam, lorazepam, buspirone, and hydroxyzine pamoate. Examples of suitable anti-proliferative agents for use in combination with the compounds of the present invention include cyclosporine A, paclitaxel, adriamycin; epithilones, cisplatin, and carboplatin. Examples of suitable anti-ulcer and gastroesophageal reflux disease agents for use in combination with the compounds of the present invention include famotidine, ranitidine, and omeprazole.

What is claimed is:
1. A compound of Formula (I)

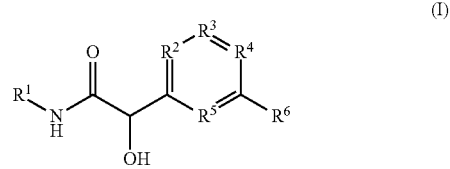

or a pharmaceutically acceptable salt thereof, wherein

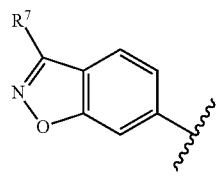

R¹ is;
R² is CH or N;
R³ is CH or N;
R⁴ is CH or N;
R⁵ is CH, N, or CR⁸
R⁶ is
  1) an aryl ring, or
  2) a heteroaryl ring, wherein the point of attachment to the heteroaryl ring is a carbon atom, and the heteroaryl ring is selected from the group consisting of:
    a) a 5- or 6-membered unsaturated monocyclic ring with 1, 2, 3, or 4 heteroatom ring atoms selected from the group consisting of N, O or S,
    b) an 9- or 10-membered unsaturated bicyclic ring with 1, 2, 3, or 4 heteroatom ring atoms selected from the group consisting of N, O or S,
said aryl and heteroaryl ring is unsubstituted, or independently mono-, di-, or tri-substituted on any carbon ring atom with R⁹;
R⁷ is —C(NR¹¹)N(R¹¹)₂, —N(R¹¹)₂, —CN or —C₁₋₆alkyl, wherein alkyl is unsubstituted or substituted at any carbon atom with —NH₂;
R⁸ is hydrogen, halogen or C₁₋₆ alkyl;
R⁹, each time in which it occurs, is independently —OCF₃, halogen, —C(O)R¹⁰, —C₁₋₆ alkyl, —N(R¹²)₂, or —CF₃;
R¹⁰ is a 6-membered heterocycle;
R¹¹, each time in which it occurs, is hydrogen or C₁₋₆ alkyl; and
R¹², each time in which it occurs, is hydrogen or C₁₋₆ alkyl.

2. A compound of claim 1, or a pharmaceutically acceptable salt thereof, wherein R¹ is

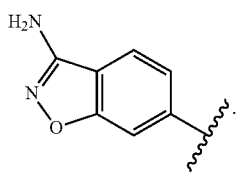 [SMILES: *c1ccc2c(N)noc2c1]

3. A compound of claim 1, or a pharmaceutically acceptable salt thereof, wherein R⁶ is

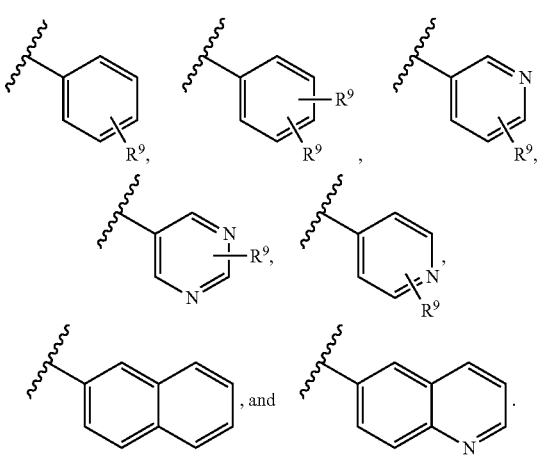

4. A compound of claim 3, or a pharmaceutically acceptable salt thereof, wherein R⁶ is

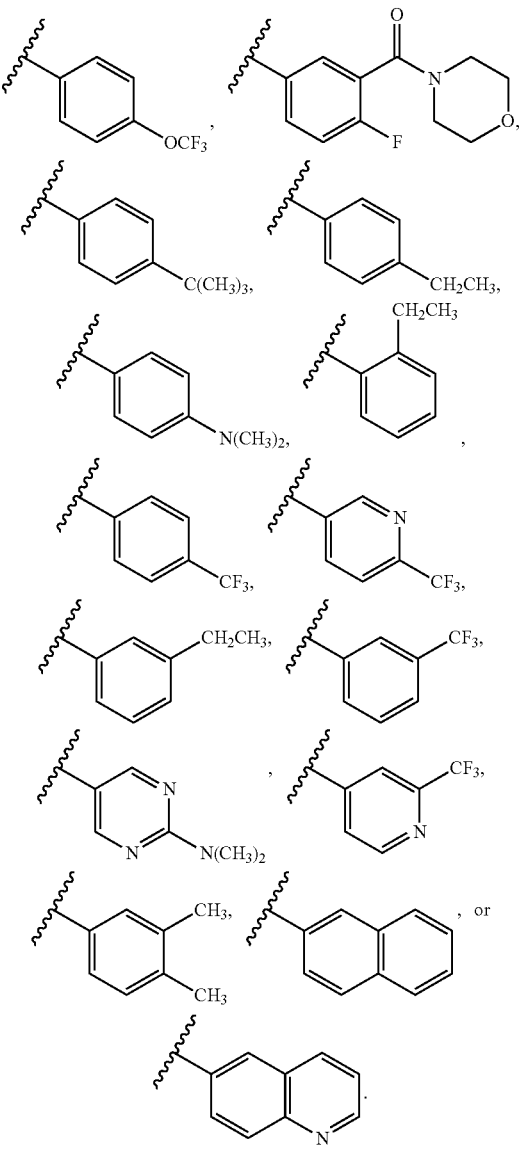

5. A compound of claim 1, or a pharmaceutically acceptable salt thereof, wherein R⁸ is hydrogen, F or —CH₃.

6. A compound of claim 1, or a pharmaceutically acceptable salt thereof, wherein R⁷ is —C(NH)NH₂, —NH₂, —CN or —CH₂NH₂.

7. A compound of claim 3, or a pharmaceutically acceptable salt thereof, wherein R⁹ is —OCF₃, F, —C(CH₃)₃, —CH₂CH₃, —CH₃, —N(CH₃)₂, —CF₃ or

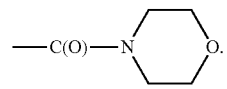

8. A compound of claim 1, or a pharmaceutically acceptable salt thereof, which is
N-(3-aminobenzo[d]isoxazol-6-yl)-2-hydroxy-2-(4'-(trifluoromethoxy) biphenyl-3-yl)acetamide,
N-(3-aminobenzo[d]isoxazol-6-yl)-2-(4'-fluoro-3'-(morpholine-4-carbonyl)biphenyl-3-yl)-2-hydroxyacetamide, N-(3-aminobenzo[d]isoxazol-6-yl)-2-(4'-tert-butylbiphenyl-3-yl)-2-hydroxyacetamide, N-(3-amino-1,2-benzisoxazol-6-yl)-2-(4'-tert-butyl-2-fluorobiphenyl-3-yl)-2-hydroxyacetamide, N-(3-amino-1,2-benzisoxazol-6-yl)-2-hydroxy-2-{6-[3-(trifluoromethyl)phenyl]pyridin-2-yl}acetamide, N-(3-amino-1,2-benzisoxazol-6-yl)-2-[6-(4-tert-butylphenyl)pyridin-2-yl]-2-hydroxyacetamide, 9. A pharmaceutical composition comprising at least one compound of claim 1, or a pharmaceutically acceptable salt thereof, and at least one pharmaceutically acceptable carrier.

10. A method of treating a thromboembolic disorder comprising administering to a patient in need thereof a therapeutically effective amount of a compound of claim 1, or a pharmaceutically acceptable salt thereof 11. The method of claim 10, wherein the thromboembolic disorder is selected from the group consisting of arterial cardiovascular thromboembolic disorders, venous cardiovascular thromboembolic disorders, and thromboembolic disorders in the chambers of the heart.

12. The method of claim 10, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

13. A pharmaceutical composition comprising: a therpeutically effective amount of at least one compound of claim 1 or a pharmaceutically acceptable salt thereof, and at least one pharmaceutically acceptable carrier, and an effective amount of at least one agent selected from the group consisting of: (a) anticoagulants, (b) anti-thrombin agents, (c) anti-platelet agents, (d) fibrinolytics, (e) hypolipidemic agents, (f) antihypertensive agents, and (g) anti-ischemic agents.

14. A pharmaceutical composition comprising: a therpeutically effective amount of at least one compound of claim 1 or a pharmaceutically acceptable salt thereof, and at least one pharmaceutically acceptable carrier, and an effective amount of at least one agent selected from the group consisting of (a-1) warfarin, (a-2) heparin, (a-3) aprotinin, (a-4) synthetic pentasaccharide, (a-5) direct acting thrombin inhibitors including hirudin and argatroban, (a-6) a factor VIIa inhibitor, (a-7) a factor VIIIa inhibitor, (a-8) a factor IXa inhbitor different from the compounds of Formula (I), (a-9) a factor Xa inhibitor, (a-10) a factor XIa inhibitor, (a-11) a thrombin inhibitor, (a-12) a TAFI, (a-13) a fibrinogen inhibitor, (b-1) a boroarginine derivative, (b-2) a boropeptide, (b-3) heparin, (b-4) hirudin, (b-5) argatroban, (c-1) a NSAID, (c-2) a IIb/IIIa antagonist, (c-3) a thromboxane-A2-receptor antagonist, (c-4) a thromboxane-A2-synthetase inhibitor, (c-5) a PDE-III inhibitor, (c-6) a PDE V inhibitor, (c-7) a ADP receptor antagonist, (c-8) an antagonist of the purinergic receptor P2Y1, (c-9) an antagonist of the purinergic receptor P2Y12, (d-1) tissue plasminogen activator (TPA, natural or recombinant) and modified forms thereof, (d-2) anistreplase, (d-3) urokinase, (d-4) streptokinase, (d-5) tenecteplase (TNK), (d-6) lanoteplase (nPA), (d-7) a factor VIIa inhibitor, (d-8) a PAI-I inhibitor, (d-9) an alpha-2-antiplasmin inhibitor, (d-10) an anisoylated plasminogen streptokinase activator complex, (e-1) a HMG-CoA reductase inhibitor, (e-2) a squalene synthetase inhibitor, (e-3) a fibrate, (e-4) a bile acid sequestrant, (e-5) an ACAT inhibitor, (e-6) a MTP inhibitor, (e-7) a lipooxygenase inhibitor, (e-8) a cholesterol absorption inhibitor, (e-9) a cholesterol ester transfer protein inhibitor, (f-1) an alpha adrenergic blocker, (f-2) a beta adrenergic blocker, (f-3) a calcium channel blocker, (f-4) a diuretic, (f-5) a renin inhibitor, (f-6) an angiotensin-converting enzyme inhibitor, (f-7) an angiotensin-II-receptor antagonist, (f-8) an ET receptor antagonist, (f-9) a Dual ET/All antagonist, (f-10) a neutral endopeptidase inhibitor, (f-11) a vasopepsidase inhibitor, (g-1) a Class I agent, (g-2) a Class II agent, (g-3) a Class III agent, (g-4) a Class IV agent, (g-5) an IAch inhibitor, (g-6) an IKur inhibitor and (g-7) a cardiac glycoside.

\* \* \* \* \*